United States Patent [19]

Russell et al.

[11] Patent Number: 5,861,248
[45] Date of Patent: Jan. 19, 1999

[54] BIOMARKERS FOR DETECTION OF PROSTATE CANCER

[75] Inventors: David W. Russell; Anice E. Thigpen, both of Dallas, Tex.

[73] Assignee: Urocor, Inc., Oklahoma City, Okla.

[21] Appl. No.: 626,169

[22] Filed: Mar. 29, 1996

[51] Int. Cl.$^6$ .............................. C12Q 1/68; C12P 19/34; C07H 19/00

[52] U.S. Cl. ........................... 435/6; 435/91.1; 435/91.2; 536/22.1; 536/23.1; 536/23.2; 536/24.32; 536/24.33

[58] Field of Search ............................. 435/6, 91.1, 91.2; 536/22.1, 23.1, 23.2, 24.31, 24.33

[56] References Cited

U.S. PATENT DOCUMENTS

| | | | |
|---|---|---|---|
| 4,800,159 | 1/1989 | Mullis et al. | 435/172.3 |
| 5,043,272 | 8/1991 | Hartley | 435/91 |
| 5,089,386 | 2/1992 | Stackebrandt et al. | 435/6 |
| 5,262,311 | 11/1993 | Pardee et al. | 435/91.2 |
| 5,312,733 | 5/1994 | Macleod | 435/69.1 |
| 5,527,884 | 6/1996 | Russell et al. | 530/350 |

FOREIGN PATENT DOCUMENTS

| | | |
|---|---|---|
| 0186522 | 7/1986 | European Pat. Off. . |
| WO 94/10343 | 5/1994 | WIPO . |
| WO 95/21944 | 8/1995 | WIPO . |
| WO 96/02002 | 1/1996 | WIPO . |

OTHER PUBLICATIONS

Sukatme et al. "a zinc finger–encoding gene coregulated with c–fos during growth and differentiation, and after cellular depolarization" Cell, vol. 53, pp. 37–43, Apr. 1988.

Cherry et al. "The internally located telomeric sequences in the germ–line chromosomes of tetrahymena are at the ends of transposon –like elements", Cell, vol. 43, pp. 747–758, Dec. 1985.

Sargent et al. "Nucleotide sequence of cloned rat serum albumin messenger RNA", Proc. Natl. Acad. Sci. USA, vol. 78, pp. 243–246, Jan. 1981.

Hunter et al. "A laminin–like adhesive protein concentrated in the synaptic cleft of the neorumuscular junction" Nature, vol. 338, pp. 229–233, Mar. 1989.

Hirt et al. "Localization and fine structure of a vaccina virus gene envelope antigen" Journal of virology, vol. 58, pp. 757–764, Jun. 1986.

Iris et al. "Dense Alu clustering and a potential new member of the NF B family within a 90 kilobase HLA class II segment", Nature Genetics, vol. 3, pp. 137–145, Feb. 1993.

Wright et al. "Expression of a zinc finger gene in HTLV–1 and HTLV–II transformed cells", Science, vol. 248, pp. 588–591, May 1990.

Nakada et al. "Influenza C virus hemagglutinn: Comparison with influenza A and B virus hemagglutinins" Journal of Virology, vol. 50, pp. 118–124, Apr. 1984.

An et al., "Sensitive, nonradioactive differential display method using chemiluminescent detection," *Biotechniques*, 20(3):342, 344 and 346, 1996.

Blok et al., "Isolation of cDNAs that are differentially expressed between androgen–dependent and androgen–independent prostate carcinoma cells using differential display PCR," *Prostate*, 26(4):231–224, 1995.

Robson et al., "Isolation of prostate androgen regulated genes using the differential display technique," *Porc. Am. Assoc. Cancer Res. Ann. Meet.*, 36:266, 1995.

(List continued on next page.)

*Primary Examiner*—Ardin H. Marschel
*Assistant Examiner*—Jezia Riley
*Attorney, Agent, or Firm*—Arnold White & Durkee

[57] ABSTRACT

Disclosed are diagnostic techniques for the detection of human prostate cancer. Genetic probes and methods useful in monitoring the progression and diagnosis of prostate cancer are described. The invention relates particularly to probes and methods for evaluating the presence of RNA species that are differentially expressed in prostate cancer compared to normal human prostate or benign prostatic hyperplasia.

15 Claims, 2 Drawing Sheets

OTHER PUBLICATIONS

An et al., "Isolation of Genes Differentially Expressed in Prostate Cancer Cells with Metastic Potential by Arbitrarily–Primed Differential Analyses (ADA)," *Proceedings of the American Association for Cancer Research*, 36:82, Mar. 1995.

Bova et al., "Homozygous Deletion and Frequent Allelic Loss of Chromosome 8p22 Loci in Human Prostate Cancer," *Cancer Research*, 53:3869–3873, Sep. 1993.

Carter and Coffey, "The Prostate: An Increasing Medical Problem," *The Prostate*, 16:39–49, 1990.

Donohue et al., "A Delayed–early Gene Activated by Fibroblast Growth Factor–1 Encodes a Protein Related to Aldose Reductase," *The Journal of Biological Chemistry*, 269(110:8604–8609, Mar. 1994.

Hastabacka et al., "The Diastroophic Dysplasia Gene Encodes a Novel Sulfate Transporter: Positional Cloning by Fine–Structure Linkage Disequilibrium Mapping," *Cell*, 78(6):1073–1087, Sep. 1994.

Isaacs et al., "Molecular Biology of Prostate Cancer," *Seminars in Oncology*, 21(5):514–521, Oct. 1994.

Liang and Pardee, "Differential Display of Eukaryotic Messenger RNA by Means of the Polymerase Chain Reaction," *Science*, 257:967–971, Aug. 1992.

Liang et al., "Differential Display and Cloning of Messenger RNAs from Human Breast Cancer versus Mammary Epithelial Cells," *Cancer Research*, 52:6966–6968, Dec. 1992.

Macoska et al., "Fluorescence in Situ Hybridization Analysis of 8p Allelic Loss and Chromosome 8 Instability in Human Prostate Cancer," *Cancer Research*, 54:3824–3830, Jul. 1994.

Mok et al., "Molecular Cloning if Differentially Expressed Genes in Human Epithelial Ovarian Cancer," *Gynecologic Oncology*, 52:247–252, 1994.

Morton et al., Multivariate Analysis of the Relationship between Survival and the Microstage of Primary Melanoma by Clark Level and Breslow Thickness, *Cancer*, 7(11):3737–3743, Jun. 1993.

Morton et al., "Reduction of E–Cadherin Levels and Deletion of the α–Carenin Gene in Human Prostate Cancer Cells," *Cencer Research*, 53:3585–3590, Aug. 1993.

Partin et al., "Nuclear Matrix Protein Patterns in Human Benign Prostatic Hyperplasia and Prostate Cancer," *Cancer Research*, 53:744–746, Feb. 1993.

Sager et al., "Identification by Differential Display of Alpha 6 Integrin as a Candidate Tumor Suppressor Gene," *The FASEB Journal*, 7:964–970, Jul. 1993.

Slamon et al., "Expression of Cellular Oncogenes in Human Malignancies," *Science*, 244:256–262, Apr. 1984.

Umbas et al., "Expression of the Cellular Adhesion Molecule E–Cadherin Is Reduced or Absent in High–Grade Prostate Cancer," *Cancer Research*, 52:5104–5109, Sep. 1992.

Wallis, "The Importance of Being Sulphated," *Current Biology*, 5(3):225–227, 1995.

Watson and Fleming, "Isolation of Differentially Expressed Sequence Tags from Human Breast Cancer," *Cancer Research*, 54:4598–4602, Sep. 1994.

Welsh et al., "Arbitrarily Primed PCR Fingerprinting of RNA," *Nucleic Acids Research*, 20(19):4965–4970, 1992.

Wong et al., "Identification of Differntially Expressed RNA in Human Ovarian Carcinoma Cells by Arbitrarily Primed PCR Fingerprinting of Total RNAs," *International Journal of Oncology*, 3:13–17, 1993.

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
( A ) LENGTH: 295 base pairs
( B ) TYPE: nucleic acid
( C ) STRANDEDNESS: single
( D ) TOPOLOGY: linear ( x i ) SEQUENCE DESCRIPTION: SEQ ID NO:1:

```
AGGAATTGGG  ATGACAAATC  CAAATCTATA  GAGTATTTGC  CTCTTAAATG  ATACCTCATT      60

GATATATTGC  ACTATTTCAT  AAATACTATA  AAATAATGAC  TAGGAAGTAA  CTTATTAAAG     120

GCTATGACTT  AAATTTGAAG  ATGAAGTACA  GTGTTCTAGG  TTTGCTGAGA  AGGCCTCATT     180

AAATTAATCT  CACTTTGAAT  ATCTCCTGAG  AGATGGACAA  TGAAATATCA  GTTGGTGGAT     240

ATGTGTGATA  GCTGATTTCA  ATATTGAAGT  ATTGAAATAA  AATATTCTTT  ACACC          295
```

( 2 ) INFORMATION FOR SEQ ID NO:2:

( i ) SEQUENCE CHARACTERISTICS:
( A ) LENGTH: 240 base pairs
( B ) TYPE: nucleic acid
( C ) STRANDEDNESS: single
( D ) TOPOLOGY: linear ( x i ) SEQUENCE DESCRIPTION: SEQ ID NO:2:

```
GGGGTGGGGG  GAACGTGGGG  GAACCTGTGT  TTCACGTGAC  TCAGAAGTGC  CCGGCGCCGT      60

CACCAGCTAT  GAATTCACCC  CGTTTCCAGT  GAGCAGATGT  CTTGCTTGGG  AAGTGGACCT     120

GTGTCTGTGT  CTGTCCTGAG  AACTTACCAG  CAGAAATCCT  TATTTCTGTG  CTACGGATTT     180

ACCAAAAATT  GTCAAGTCTT  TTTCAGTTTA  ACAGTTCCTT  TACATGTGTA  GTATTTGAGG     240
```

( 2 ) INFORMATION FOR SEQ ID NO:3:

( i ) SEQUENCE CHARACTERISTICS:
( A ) LENGTH: 394 base pairs
( B ) TYPE: nucleic acid
( C ) STRANDEDNESS: single
( D ) TOPOLOGY: linear ( x i ) SEQUENCE DESCRIPTION: SEQ ID NO:3:

```
CAGATACCCC  GAAGCCATGG  CAAGCAAGGG  CTTGCAGGAC  CTGAAGCAAC  AGGTGGAGGG      60
```

| | | | | | | |
|---|---|---|---|---|---|---|
| GACCGCCCAG | GAAGCCGTGT | CAGCGGCCGG | AGCGGCAGCT | CAGCAAGTGG | TGGACCAGGC | 120 |
| CACAGAGGCG | GGGCAGAAAG | CCATGGACCA | GCTGGCCAAG | ACCACCCAGG | AAACCATCGA | 180 |
| CAAGACTGCT | AACCAGGCCT | CTGACACCTT | CTCTGGGATT | GGGAAAAAAT | TCGGCCTCCT | 240 |
| GAAATGACAG | CAGGGAGACT | TGGGTCGGCC | TCCTGAAATG | ACAGCAGGGA | GACTTGGGTG | 300 |
| ACCCCCCTCC | CAGGCGCCAT | CTAGCACAGC | CTGGCCCTGA | TCTCCGGGCA | GCCGCCACCT | 360 |
| CCTCGGTCTG | CCCCCTCATT | AAAATTCACG | TTCC | | | 394 |

( 2 ) INFORMATION FOR SEQ ID NO:4:

( i ) SEQUENCE CHARACTERISTICS:
        ( A ) LENGTH: 221 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

| | | | | | | |
|---|---|---|---|---|---|---|
| GCCCAGTGCT | CATAAATAGT | CTGTTCACAT | CCTGCTTTCT | GTTCCAATCT | TTTCGTCTCT | 60 |
| CCTTTTGGTT | GTTACAACTG | ATCTATCTTT | GAGATTTTTC | ACTCTTCAAA | TGTCCCAGAA | 120 |
| TTTCCTGCCT | CCAAAATCAT | GAAGAGATAT | TTCAGATCTC | AGAGATTCCT | TATACCAATA | 180 |
| ATGCCACTTT | GGGCTGCAGC | AAATATGTAG | TTTTCCCCAC | A | | 221 |

( 2 ) INFORMATION FOR SEQ ID NO:5:

( i ) SEQUENCE CHARACTERISTICS:
        ( A ) LENGTH: 189 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

| | | | | | | |
|---|---|---|---|---|---|---|
| ATGCATGAGG | AAAAAGCGAG | AGAAAAGGAA | AAGCCAACAG | GCCCCCCAGC | CAAGAAAGCT | 60 |
| ATCTCTGAGT | TGCCCTGATT | TGAAGGGAAA | AGGGATGATG | GGATTGAAGG | GGCTTCTAAT | 120 |
| GTCCAGATA | TGGAAACAGA | AGACAAAATT | GTAAGCCAGA | GTCAACAAAT | TAAATAAATT | 180 |
| ACCCCCTCC | | | | | | 189 |

( 2 ) INFORMATION FOR SEQ ID NO:6:

( i ) SEQUENCE CHARACTERISTICS:
        ( A ) LENGTH: 272 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

| | | | | | | |
|---|---|---|---|---|---|---|
| GGAGGAGGAG | ATGGCCATAG | GAGAGGAGGG | TTCCTCTTAG | GTCAGATGGA | GGTTCTCAGA | 60 |
| GCCAAGTCCT | CCCTCTCTAC | TGGAGTGGAA | GGTCTATTGG | ACAACAATCC | TTTCTGCCCA | 120 |
| CTTCCCCTTC | CCCAATTACT | ATTCCCTTTG | ACTTCAGCTG | CTGAAACAGC | CATGTCCAAG | 180 |
| TTCTTCACCT | CTATCCAAAG | AACTTGATTT | GCATGGATTT | TGGATAAATC | ATTTCAGTAT | 240 |
| CATCTCCATC | ATATGCCTGA | CCCCTTGCTC | CC | | | 272 |

( 2 ) INFORMATION FOR SEQ ID NO:7:

( i ) SEQUENCE CHARACTERISTICS:
        ( A ) LENGTH: 353 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

| | | | | | |
|---|---|---|---|---|---|
| AACACAGCAA | AAAATATAAT | TCCAGCCAAA | GATTCTGGAA | AATCCCTCAG | AAGGAGGGAT | 60
| AACAGGATTT | GACCTTTACC | AGCGATTTCT | GTCCATATGT | GGATGTAAAC | AGTTCTGGAA | 120
| CGTTATGCAT | GCAGTTAGCG | AATCCTTGAA | TTATGTTCTG | GTTTGTACTT | GTCCCATCCA | 180
| TCCAAACAAG | AGATTCTGCT | TTTGGTAGCC | ATCTGTAGAA | ACATTTAAGA | TGTCACTAGA | 240
| ATTTACATTT | CATCCTCTCT | ACTTGGGTTG | AGGTTGCCTA | TACTTGCATA | TTGTTAAAAT | 300
| GTTTTGGTTG | CTGATATTCA | GAGGAATGAA | ACCTGGAACC | AAAGCCTAAT | TTG | 353

( 2 ) INFORMATION FOR SEQ ID NO:8:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

CCAGGATCCA GCATTTTGCT GCTTTATCAA AATGG        35

( 2 ) INFORMATION FOR SEQ ID NO:9:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

ACCGGTACCT CACAAGGAGC TGTGAATGAG G        31

( 2 ) INFORMATION FOR SEQ ID NO:10:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

CCGCCGTCCT TCAATTTTCT TCACACTATC AACA        34

( 2 ) INFORMATION FOR SEQ ID NO:11:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

GTCGGTGGTA TCTCCTAGTA ACCAAACCTA CA        32

( 2 ) INFORMATION FOR SEQ ID NO:12:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

ATGGCCGCGG CCAAGGCCGA GATGC        25

( 2 ) INFORMATION FOR SEQ ID NO:13:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:13:

AGGGTAGGCA GGAGGCGGGT ACTGGAG   27

( 2 ) INFORMATION FOR SEQ ID NO:14:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:14:

CATCCTGAGA GCCAGCCTGA CATTAGA   27

( 2 ) INFORMATION FOR SEQ ID NO:15:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:15:

CCTCCTGCAT AATAGCTTTA GGTGACTTGA AGA   33

( 2 ) INFORMATION FOR SEQ ID NO:16:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:16:

CGAGCTGCCT GACGGCCAGG TCATC   25

( 2 ) INFORMATION FOR SEQ ID NO:17:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:17:

GAAGCATTTG CGGTGGACGA TGGAG   25

( 2 ) INFORMATION FOR SEQ ID NO:18:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:18:

ACATTGAAGC ACTCCGCGAC   20

( 2 ) INFORMATION FOR SEQ ID NO:19:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:19:

AGAGTGGCAG CAACCAAGCT        20

BIOMARKERS FOR DETECTION OF PROSTATE CANCER

BACKGROUND OF THE INVENTION

A. Field of the Invention

The present invention relates generally to nucleic acid sequences useful as probes for the diagnosis of cancer and methods relating thereto. More particularly, the present invention concerns probes and methods useful in diagnosis, identifying and monitoring the progression of diseases of the prostate through measurements of gene products.

B. Description of the Related Art

Carcinoma of the prostate (PCA) is the second-most frequent cause of death in men in the United States (Boring, 1993). The increased incidence of prostate cancer during the last decade has established prostate cancer as the most prevalent of all cancers (Carter and Coffey, 1990). Although prostate cancer is the most common cancer found in United States men, (approximately 200,000 newly diagnosed cases/year), the molecular changes underlying its genesis and progression remain poorly understood (Boring et al., 1993). According to American Cancer Society estimates, the number of deaths from PCA is increasing in excess of 8% annually.

An unusual challenge presented by prostate cancer is that most prostate tumors do not represent life threatening conditions. Evidence from autopsies indicate that 11 million American men have prostate cancer (Dbom, 1983). These figures are consistent with prostate carcinoma having a protracted natural history in which relatively few tumors progress to clinical significance during the lifetime of the patient. If the cancer is well-differentiated, organ-confined and focal when detected, treatment does not extend the life expectancy of older patients.

Unfortunately, the relatively few prostate carcinomas that are progressive in nature are likely to have already metastasized by the time of clinical detection. Survival rates for individuals with metastatic prostate cancer are quite low. Between these two extremes are patients with prostate tumors that will metastasize but have not yet done so. For these patients, surgical removal of their prostates is curative and extends their life expectancy. Therefore, determination of which group a newly diagnosed patient falls within is critical in determining optimal treatment and patient survival.

Although clinical and pathologic stage and histological grading systems (e.g., Gleason's) have been used to indicate prognosis for groups of patients based on the degree of tumor differentiation or the type of glandular pattern (Carter and Coffey, 1989; Diamond et al., 1982), these systems do not predict the progression rate of the cancer. While the use of computer-system image analysis of histologic sections of primary lesions for "nuclear roundness" has been suggested as an aide in the management of individual patients (Diamond et al., 1982), this method is of limited use in studying the progression of the disease.

Recent studies have identified several recurring genetic changes in prostate cancer including: 1) allelic loss (particularly loss of chromosome 8p and 16q) (Bova, et al., 1993; Macoska et al., 1994; Carter et al., 1990); 2) generalized DNA hypermethylation (Isaacs et al., 1994); 3) point mutations or deletions of the retinoblastoma (Rb) and p53 genes (Bookstein et al., 1990a; Bookstein et al., 1990b; Isaacs et al., 1991); 4) alterations in the level of certain cell-cell adhesion molecules (i.e., E-cadherin/alpha-catenin) (Carter et al., 1990; Morton et al., 1993; Umbas et al., 1992) and aneuploidy and aneusomy of chromosomes detected by fluorescence in situ hybridization (FISH), particularly chromosomes 7 and 8 (Macoska et al., 1994; Visakorpi et al., 1994; Takahashi et al., 1994; Alcaraz et al., 1994).

The analysis of DNA content/ploidy using flow cytometry and FISH has been demonstrated to have utility predicting prostate cancer aggressiveness (Pearsons et al., 1993; Macoska et al., 1994; Visakorpi et al., 1994; Takahashi et al., 1994; Alcaraz et al., 1994; Pearsons et al., 1993), but these methods are expensive, time-consuming, and the latter methodology requires the construction of centromere-specific probes for analysis.

Specific nuclear matrix proteins have been reported to be associated with prostate cancer (Partin et al., 1993). However, these protein markers apparently do not distinguish between benign prostate hyperplasia and prostate cancer (Partin et al., 1993). Unfortunately, markers that cannot distinguish between benign and malignant prostate tumors are of little value.

It is known that the processes of transformation and tumor progression are associated with changes in the levels of messenger RNA species (Slamon et al., 1984; Sager et al., 1993; Mok et al., 1994; Watson et al., 1994). Recently, a variation on polymerase chain reaction (PCR) analysis, known as RNA fingerprinting or differential display PCR, has been used to identify messages differentially expressed in ovarian or breast carcinomas (Liang et al., 1992; Sager et al., 1993; Mok et al., 1994; Watson et al., 1994). By using arbitrary primers to generate "fingerprints" from total cell RNA, followed by separation of the amplified fragments by high resolution gel electrophoresis, it is possible to identify RNA species that are either up-regulated or down-regulated in cancer cells. Results of these studies indicate the presence of several markers of potential utility for diagnosis of breast or ovarian cancer, including a6-integrin (Sager et al., 1993), DEST001 and DEST002 (Watson et al., 1994), and LF4.0 (Mok et al., 1994).

There remain, however, deficiencies in the prior art with respect to the identification of the genes linked with the progression of prostate cancer and the development of diagnostic methods to monitor disease progression. Likewise, the identification of genes that are differentially expressed in prostate cancer would be of considerable importance in the development of a rapid, inexpensive method to diagnose prostate cancer.

SUMMARY OF THE INVENTION

The present invention addresses deficiencies in the prior art by identifying and characterizing RNA species that are differentially expressed in human prostate cancers, along with providing methods for identifying such RNA species. These RNA species and the corresponding encoded protein species have utility, for example, as markers of prostate disease and as targets for therapeutic intervention in prostate disease.

The identified markers of prostate disease can in turn be used to design specific oligonucleotide probes and primers. When used in combination with nucleic acid amplification procedures, these probes and primers permit the rapid analysis of prostate biopsy core specimens. This analysis will assist physicians in diagnosing prostate cancer and determining optimal treatment courses for individuals with prostate tumors of varying malignancy. The same probes and primers can be used for in situ hybridization or in situ PCR detection and diagnosis of prostate cancer.

The identified markers of prostate disease can also be used to identify and isolate fall length gene sequences, including regulatory elements for gene expression, from genomic human DNA libraries. The cDNA sequences identified in the present invention can be used as hybridization probes to screen genomic human DNA libraries by standard techniques. Once partial genomic clones have been identified, full-length genes can be isolated by "chromosomal walking" (also called "overlap hybridization"). See, Chinault & Carbon "Overlap Hybridization Screening: Isolation and Characterization of Overlapping DNA Fragments Surrounding the LEU2 Gene on Yeast Chromosome III." Gene 5:111–126, 1979. Once a partial genomic clone has been isolated using a cDNA hybridization probe, nonrepetitive segments at or near the ends of the partial genomic clone may be used as hybridization probes in further genomic library screening, ultimately allowing the isolation of entire gene sequences for the cancer markers of interest. Those experienced in the art will realize that full length genes may be obtained using the small expressed sequence tags (ESTs) described in this patent using technology currently available and described in this patent (Sambrook et al., 1989; Chinault & Carbon, 1979).

The identified markers can be used to identify and isolate cDNA sequences. The EST sequences identified in the present invention can be used as hybridization probes to screen human cDNA libraries by standard techniques. Those experienced in the art will realize that these techniques would start by obtaining a high quality human cDNA library, many of which are readily available from commercial or other sources. The library would be plated on, for example, agarose plates containing nutrients, antibiotics and other standard ingredients. Individual colonies would be transferred to nylon or nitrocellulose membranes and the EST probes would be hybridized to complementary sequences on the membranes. Hybridization would be detected by radioactive or enzyme-linked tags associated with the hybridized probes. Positive colonies would be grown up and sequenced by, for example, Sanger dideoxynucleotide sequencing or similar methods well known in the art. Comparison of cloned cDNA sequences with known human or animal cDNA or genomic sequences can be performed using computer programs and databases well known to the skilled practitioner.

In one embodiment of the present invention, the isolated nucleic acids are incorporated into expression vectors and expressed as the encoded proteins or peptides. Such proteins or peptides are in turn used as antigens for induction of monoclonal or polyclonal antibody production.

In another embodiment of the present invention, the aforementioned oligonucleotide hybridization probes and primers are specific for markers of prostate disease selected from the group comprising SEQ ID NO:1, SEQ ID NO:2, SEQ ID NO:3, SEQ ID NO:4, SEQ ID NO:5, SEQ ID NO:6, SEQ ID NO:7, Egr1 (encoding the protein corresponding to GenBank Accession number P18146) and DTDST (GenBank Accession numbers U14528 and D42049). The availability of probes and primers specific for such unique markers provides the basis for diagnostic kits identifying metastatic tumor progression in prostate cancer patients.

An embodiment of the present invention encompasses a kit for use in detecting prostate cancer cells in a biological sample comprising pairs of primers for amplifying nucleic acids corresponding to the marker genes and containers for each of these primers. In another embodiment, the invention encompasses a kit for use in detecting prostate cancer cells in a biological sample comprising oligonucleotide probes that bind with high affinity to markers of prostate disease and containers for each of these probes. In a further embodiment, the invention encompasses a kit for use in detecting prostate cancer cells in a biological sample comprising antibodies specific for proteins encoded by the nucleic acid markers of prostate disease identified in the present invention.

Other embodiments of the invention include methods for treating prostate cancer patients by administration of effective amounts of antibodies specific for the peptide products of prostate cancer markers or by administration of effective amounts of vectors producing anti-sense messenger RNAs that bind to the nucleic acid products of prostate cancer markers, thereby inhibiting expression of the protein products of prostate cancer marker genes.

The present invention comprises an isolated nucleic acid selected from the group consisting of SEQ ID NO:1, SEQ ID NO:2, SEQ ID NO:3, SEQ ID NO:4, SEQ ID NO:5, SEQ ID NO:6 and SEQ ID NO:7. The invention further comprises an isolated nucleic acid of between 17 and 100 bases in length, either identical to or complementary with portions of the above mentioned isolated nucleic acids.

The present invention comprises proteins and peptides with amino acid sequences encoded by the aforementioned isolated nucleic acids. The invention also comprises methods for identifying biomarkers for prognostic or diagnostic assays of human prostate disease, using the techniques of RNA fingerprinting to identify RNAs that are differentially expressed between prostate cancers versus normal or benign prostate.

The invention further comprises methods for detecting prostate cancer cells in biological samples, using nucleic acid amplification techniques with primers and hybridization probes selected to bind specifically to an isolated nucleic acid selected from the group comprising SEQ ID NO:1, SEQ ID NO:2, SEQ ID NO:3, SEQ ID NO:4, SEQ ID NO:5, SEQ ID NO:6, SEQ ID NO:7, Egr1, and DTDST, thereby measuring the amounts of nucleic acid amplification products formed.

The invention further comprises the prognosis and/or diagnosis of prostate cancer by measuring the amounts of nucleic acid amplification products formed. The invention comprises methods of treating individuals with prostate cancer by providing effective amounts of antibodies and/or antisense DNA molecules which bind to the products of the above mentioned isolated nucleic acids. The invention further comprises kits for performing the above-mentioned procedures, containing amplification primers and/or hybridization probes.

The present invention further comprises production of antibodies specific for proteins or peptides encoded by SEQ ID NO:1, SEQ ID NO:2, SEQ ID NO:3, SEQ ID NO:4, SEQ ID NO:5, SEQ ID NO:6, SEQ ID NO:7, Egr1 , or DTDST, and the use of those antibodies for diagnostic applications in detecting prostate cancer. The invention further comprises therapeutic treatment of prostate cancer by administration of effective doses of inhibitors specific for the aforementioned encoded proteins.

DETAILED DESCRIPTION OF THE PREFERRED EMBODIMENTS

Figure 1:
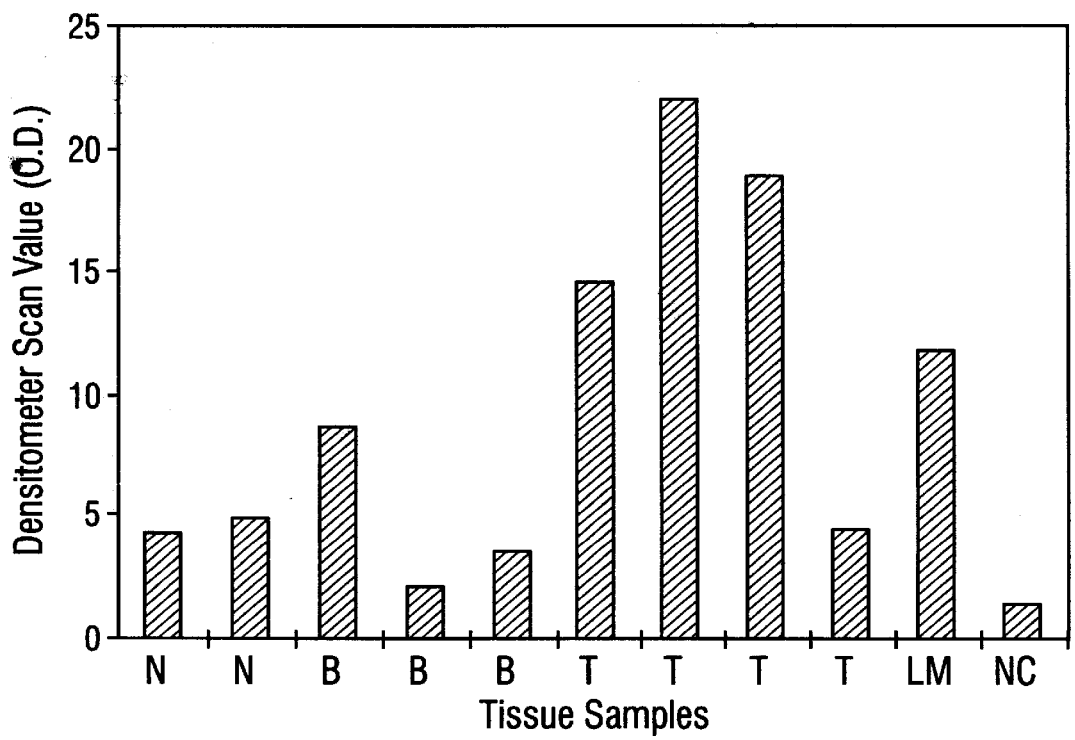
FIG. 1. Normalized quantitative RT-PCR of E22B135 shows that it is overexpressed in prostate cancers compared with normal and benign prostate tissues. The densitometric scanning data were normalized against β-actin mRNA. N=normal prostate, B=benign prostatic hyperplasia (BPH), NB=needle core biopsy of prostate cancer, T=primary prostate cancer, LM=metastatic lymph node prostate cancer, NC=negative control.

The present invention concerns the early detection, diagnosis, prognosis and treatment of prostate diseases, such as prostate cancer or benign prostatic hyperplasia (BPH). Markers of prostate disease, in the form of nucleic acid sequences isolated from human prostate tumors or prostate cancer cell lines, are disclosed. These markers are indicators of malignant transformation of prostate tissues and are diagnostic of the potential for metastatic spread of malignant prostate tumors.

Those skilled in the art will realize that the nucleic acid sequences disclosed will find utility in a variety of applications in prostate cancer detection, diagnosis, prognosis and treatment. Examples of such applications within the scope of the present invention comprise amplification of markers of prostate disease using specific primers, detection of markers of prostate disease by hybridization with oligonucleotide probes, incorporation of isolated nucleic acids into vectors, expression of vector-incorporated nucleic acids as RNA and protein, development of immunologic reagents corresponding to marker encoded products, and therapeutic treatments of prostate cancer using antibodies, anti-sense nucleic acids, or other inhibitors specific for the identified prostate cancer markers.

A. Nucleic Acids

As described in Example 1, the present invention discloses nine markers of prostate disease, identified by RNA fingerprinting. These include seven previously unknown gene products, as well as nucleic acid products of the Egr1 and DTDST genes. The latter two gene products have been previously identified in other disease states, but the present invention is the first report of their overexpression in prostate cancer.

In one embodiment, the nucleic acid sequences disclosed herein find utility as hybridization probes or amplification primers. In certain embodiments, these probes and primers consist of oligonucleotide fragments. Such fragments should be of sufficient length to provide specific hybridization to an RNA or DNA sample extracted from tissue. The sequences typically will be 10–20 nucleotides, but may be longer. Longer sequences, e.g., 40, 50, 100, 500 and even up to full length, are preferred for certain embodiments.

Nucleic acid molecules having contiguous stretches of about 10, 15, 17, 20, 30, 40, 50, 60, 75 or 100 or 500 nucleotides from a sequence selected from the group comprising SEQ ID NO:1, SEQ ID NO:2, SEQ ID NO:3, SEQ ID NO:4, SEQ ID NO:5, SEQ ID NO:6, SEQ ID NO:7, Egr1 and DTDST are contemplated. Molecules that are complementary to the above mentioned sequences and that bind to these sequences under high stringency conditions also are contemplated. These probes will be useful in a variety of hybridization embodiments, such as Southern and northern blotting. In some cases, it is contemplated that probes may be used that hybridize to multiple target sequences without compromising their ability to effectively diagnose cancer. In certain embodiments, it is contemplated that multiple probes may be used for hybridization to a single sample.

Various probes and primers can be designed around the disclosed nucleotide sequences. Primers may be of any length but, typically, are 10–20 bases in length. By assigning numeric values to a sequence, for example, the first residue is 1, the second residue is 2, etc., an algorithm defiring all primers can be proposed:

n to n+y where n is an integer from 1 to the last number of the sequence and y is the length of the primer minus one (9 to 19), where n+y does not exceed the last number of the sequence. Thus, for a 10-mer, the probes correspond to bases 1 to 10, 2 to 11, 3 to 12 . . . and so on. For a 15-mer, the probes correspond to bases 1 to 15, 2 to 16, 3 to 17 . . . and so on. For a 20-mer, the probes correspond to bases 1 to 20, 2 to 21, 3 to 22 . . . and so on.

The values of n in the algorithm above for each of the nucleic acid sequences is: SEQ ID NO:1, n=295; SEQ ID NO:2, n=240; SEQ ID NO:3, n=394; SEQ ID NO:4, n=221; SEQ ID NO:5, n=189; SEQ ID NO:6, n=272; and SEQ ID NO:7, n=353.

The use of a hybridization probe of between 17 and 100 nucleotides in length allows the formation of a duplex molecule that is both stable and selective. Molecules having complementary sequences over stretches greater than 20 bases in length are generally preferred, in order to increase stability and selectivity of the hybrid, and thereby improve the quality and degree of particular hybrid molecules obtained. One will generally prefer to design nucleic acid molecules having stretches of 20 to 30 nucleotides, or even longer where desired. Such fragments may be readily prepared by, for example, directly synthesizing the fragment by chemical means or by introducing selected sequences into recombinant vectors for recombinant production.

Accordingly, the nucleotide sequences of the invention may be used for their ability to selectively form duplex molecules with complementary stretches of genes or RNAs or to provide primers for amplification of DNA or RNA from tissues. Depending on the application envisioned, one will desire to employ varying conditions of hybridization to achieve varying degrees of selectivity of probe towards target sequence.

For applications requiring high selectivity, one will typically desire to employ relatively stringent conditions to form the hybrids, e.g., one will select relatively low salt and/or high temperature conditions, such as provided by about 0.02M to about 0.10M NaCl at temperatures of about 50° C. to about 70° C. Such high stringency conditions tolerate little, if any, mismatch between the probe and the template or target strand, and would be particularly suitable for isolating specific genes or detecting specific mRNA transcripts. It is generally appreciated that conditions can be rendered more stringent by the addition of increasing amounts of formamide.

For certain applications, for example, substitution of amino acids by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25M NaCl at temperatures of about 37° C. to about 55° C., while a low stringency condition could be provided by about 0.15M to about 0.9M salt, at temperatures ranging from about 20° C. to about 55° C. Thus, hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means visible to the human eye or spectrophotometrically, to identify specific hybridization with complementary nucleic acid-containing samples.

In general, it is envisioned that the hybridization probes described herein will be useful both as reagents in solution hybridization, as in PCR, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface to remove non-specifically bound probe molecules, hybridization is detected, or even quantified, by means of the label.

It will be understood that this invention is not limited to the particular probes disclosed herein and particularly is intended to encompass at least nucleic acid sequences that are hybridizable to the disclosed sequences or are functional analogs of these sequences.

For applications in which the nucleic acid segments of the present invention are incorporated into vectors, such as plasmids, cosmids or viruses, these segments may be combined with other DNA sequences, such as promoters, polyadenylation signals, restriction enzyme sites, multiple cloning sites, other coding segments, and the like, such that their overall length may vary considerably. It is contemplated that a nucleic acid fragment of almost any length may be employed, with the total length preferably being limited by the ease of preparation and use in the intended recombinant DNA protocol.

DNA segments encoding a specific gene may be introduced into recombinant host cells and employed for expressing a specific structural or regulatory protein. Alternatively, through the application of genetic engineering techniques, subportions or derivatives of selected genes may be employed. Upstream regions containing regulatory regions such as promoter regions may be isolated and subsequently employed for expression of the selected gene.

B. Encoded Proteins

Once the entire coding sequence of a marker-associated gene has been determined, the gene can be inserted into an appropriate expression system. The gene can be expressed in any number of different recombinant DNA expression systems to generate large amounts of the polypeptide product, which can then be purified and used to vaccinate animals to generate antisera with which further studies may be conducted.

Examples of expression systems known to the skilled practitioner in the art include bacteria such as *E. coli,* yeast such as *Saccharomyces cerevisia* and *Pichia pastoris,* baculovirus, and mammalian expression systems such as in Cos or CHO cells. In one embodiment, polypeptides are expressed in *E. coli* and in baculovirus expression systems. A complete gene can be expressed or, alternatively, fragments of the gene encoding portions of polypeptide can be produced.

In one embodiment, the gene sequence encoding the polypeptide is analyzed to detect putative transmembrane sequences. Such sequences are typically very hydrophobic and are readily detected by the use of standard sequence analysis software, such as MacVector (IBI, New Haven, Conn.). The presence of transmembrane sequences is often deleterious when a recombinant protein is synthesized in many expression systems, especially *E. coli,* as it leads to the production of insoluble aggregates that are difficult to renature into the native conformation of the protein. Deletion of transmembrane sequences typically does not significantly alter the conformation of the remaining protein structure.

Moreover, transmembrane sequences, being by definition embedded within a membrane, are inaccessible. Therefore, antibodies to these sequences will not prove useful for in vivo or in situ studies. Deletion of transmembrane-encoding sequences from the genes used for expression can be achieved by standard techniques. For example, fortuitously-placed restriction enzyme sites can be used to excise the desired gene fragment, or PCR-type amplification can be used to amplify only the desired part of the gene. The skilled practitioner will realize that such changes must be designed to not change the translational reading frame for downstream portions of the protein-encoding sequence.

In one embodiment, computer sequence analysis is used to determine the location of the predicted major antigenic determinant epitopes of the polypeptide. Software capable of carrying out this analysis is readily available commercially, for example MacVector (IBI, New Haven, Conn.). The software typically uses standard algorithms such as the Kyte/Doolittle or Hopp/Woods methods for locating hydrophilic sequences which are characteristically found on the surface of proteins and are, therefore, likely to act as antigenic determinants.

Once this analysis is made, polypeptides can be prepared that contain at least the essential features of the antigenic determinant and that can be employed in the generation of antisera against the polypeptide. Minigenes or gene fusions encoding these determinants can be constructed and inserted into expression vectors by standard methods, for example, using PCR methodology.

The gene or gene fragment encoding a polypeptide can be inserted into an expression vector by standard subcloning techniques. In one embodiment, an *E. coli* expression vector is used that produces the recombinant polypeptide as a fusion protein, allowing rapid affinity purification of the protein. Examples of such fusion protein expression systems are the glutathione S-transferase system (Pharmacia, Piscataway, N.J.), the maltose binding protein system (NEB, Beverley, Mass.), the FLAG system (IBI, New Haven, Conn.), and the 6xHis system (Qiagen, Chatsworth, Calif.).

Some of these systems produce recombinant polypeptides bearing only a small number of additional amino acids, which are unlikely to affect the antigenic ability of the recombinant polypeptide. For example, both the FLAG system and the 6xHis system add only short sequences, both of that are known to be poorly antigenic and which do not adversely affect folding of the polypeptide to its native conformation. Other fusion systems produce polypeptide where it is desirable to excise the fusion partner from the desired polypeptide. In one embodiment, the fusion partner is linked to the recombinant polypeptide by a peptide sequence containing a specific recognition sequence for a protease. Examples of suitable sequences are those recognized by the Tobacco Etch Virus protease (Life Technologies, Gaithersburg, Md.) or Factor Xa (New England Biolabs, Beverley, Mass.).

In another embodiment, the expression system used is one driven by the baculovirus polyhedron promoter. The gene encoding the polypeptide can be manipulated by standard techniques in order to facilitate cloning into the baculovirus vector. One baculovirus vector is the pBlueBac vector (Invitrogen, Sorrento, Calif.). The vector carrying the gene for the polypeptide is transfected into *Spodoptera frugiperda* (Sf9) cells by standard protocols, and the cells are cultured and processed to produce the recombinant antigen. See Summers et al., A MANUAL OF METHODS FOR BACULOVIRUS VECTORS AND INSECT CELL CULTURE PROCEDURES, Texas Agricultural Experimental Station.

As an alternative to recombinant polypeptides, synthetic peptides corresponding to the antigenic determinants can be prepared. Such peptides are at least six amino acid residues long, and may contain up to approximately 35 residues, which is the approximate upper length limit of automated peptide synthesis machines, such as those available from Applied Biosystems (Foster City, Calif.). Use of such small peptides for vaccination typically requires conjugation of the peptide to an immunogenic carrier protein such as hepatitis B surface antigen, keyhole limpet hemocyanin or bovine serum albumin. Methods for performing this conjugation are well known in the art.

In one embodiment, amino acid sequence variants of the polypeptide can be prepared. These may, for instance, be minor sequence variants of the polypeptide that arise due to natural variation within the population or they may be homologues found in other species. They also may be sequences that do not occur naturally but that are sufficiently similar that they function similarly and/or elicit an immune response that cross-reacts with natural forms of the polypeptide. Sequence variants can be prepared by standard methods of site-directed mutagenesis such as those described below in the following section.

Amino acid sequence variants of the polypeptide can be substitutional, insertional or deletion variants. Deletion variants lack one or more residues of the native protein which are not essential for function or immunogenic activity, and are exemplified by the variants lacking a transmembrane sequence described above. Another common type of deletion variant is one lacking secretory signal sequences or signal sequences directing a protein to bind to a particular part of a cell. An example of the latter sequence is the SH2 domain, which induces protein binding to phosphotyrosine residues.

Substitutional variants typically contain the exchange of one amino acid for another at one or more sites within the protein, and may be designed to modulate one or more properties of the polypeptide such as stability against proteolytic cleavage. Substitutions preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

Insertional variants include fusion proteins such as those used to allow rapid purification of the polypeptide and also can include hybrid proteins containing sequences from other proteins and polypeptides which are homologues of the polypeptide. For example, an insertional variant could include portions of the amino acid sequence of the polypeptide from one species, together with portions of the homologous polypeptide from another species. Other insertional variants can include those in which additional amino acids are introduced within the coding sequence of the polypeptide. These typically are smaller insertions than the fusion proteins described above and are introduced, for example, into a protease cleavage site.

In one embodiment, major antigenic determinants of the polypeptide are identified by an empirical approach in which portions of the gene encoding the polypeptide are expressed in a recombinant host, and the resulting proteins tested for their ability to elicit an immune response. For example, PCR can be used to prepare a range of cDNAs encoding peptides lacking successively longer fragments of the C-terminus of the protein. The immunoprotective activity of each of these peptides then identifies those fragments or domains of the polypeptide that are essential for this activity. Further experiments in which only a small number of amino acids are removed at each iteration then allows the location of the antigenic determinants of the polypeptide.

Another embodiment for the preparation of the polypeptides according to the invention is the use of peptide mimetics. Mimetics are peptide-containing molecules that mimic elements of protein secondary structure. See, for example, Johnson et al.,"Peptide Turn Mimetics" in *BIOTECHNOLOGY AND PHARMACY,* Pezzuto et al., Eds., Chapman and Hall, New York (1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule.

Successful applications of the peptide mimetic concept have thus far focused on mimetics of b-turns within proteins, which are known to be highly antigenic. Likely b-turn structure within an polypeptide can be predicted by computer-based algorithms as discussed above. Once the component amino acids of the turn are determined, peptide mimetics can be constructed to achieve a similar spatial orientation of the essential elements of the amino acid side chains.

Modification and changes may be made in the structure of a gene and still obtain a functional molecule that encodes a protein or polypeptide with desirable characteristics. The following is a discussion based upon changing the amino acids of a protein to create an equivalent, or even an improved, second-generation molecule. The amino acid changes may be achieved by change the codons of the DNA sequence, according to the following data.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and its underlying DNA coding sequence, and nevertheless obtain a protein with like properties. It is thus contemplated by the inventors that various changes may be made in the DNA sequences of genes without appreciable loss of their biological utility or activity.

In making such changes, the hydropathic index of amino acids may be considered. The importance of the hydropathic amino acid index in conferring interactive biologic function on a protein is generally understood in the art (Kyte & Doolittle, 1982).

| Amino Acids | | | Codons | | | |
|---|---|---|---|---|---|---|
| Alanine | Ala | A | GCA | GCC | GCG | GCU |
| Cysteine | Cys | C | UGC | UGU | | |
| Aspartic acid | Asp | D | GAC | GAU | | |
| Glutamic acid | Glu | E | GAA | GAG | | |
| Phenylalanine | Phe | F | UUC | UUU | | |
| Glycine | Gly | G | GGA | GGC | GGG | GGU |
| Histidine | His | H | CAC | CAU | | |
| Isoleucine | Ile | I | AUA | AUC | AUU | |
| Lysine | Lys | K | AAA | AAG | | |
| Leucine | Leu | L | UUA | UUG | CUA | CUC | CUG | CUU |
| Methionine | Met | M | AUG | | | |
| Asparagine | Asn | N | AAC | AAU | | |
| Proline | Pro | P | CCA | CCC | CCG | CCU |
| Glutamine | Gln | Q | CAA | CAG | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU |
| Valine | Val | V | GUA | GUC | GUG | GUU |
| Tryptophan | Trp | W | UGG | | | |
| Tyrosine | Tyr | Y | UAC | UAU | | |

It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (kyte & Doolittle, 1982), these are: Isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

C. Site-Specific Mutagenesis

Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art. As will be appreciated, the technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired protein. An oligonucleotide primer bearing the desired mutated sequence is synthetically prepared. This primer is then annealed with the single-stranded DNA preparation, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

D. Preparation of Antibodies Specific for Encoded Proteins

1. Expression of Proteins from Cloned cDNAs

The cDNA species specified in SEQ ID NO:1, SEQ ID NO:2, SEQ ID NO:3, SEQ ID NO:4, SEQ ID NO:5, SEQ ID NO:6, SEQ ID NO:7, Egr1 and DTDST can be expressed as encoded peptides or proteins. The engineering of DNA segment(s) for expression in a prokaryotic or eukaryotic system may be performed by techniques generally known to those of skill in recombinant expression. It is believed that virtually any expression system may be employed in the expression of the claimed nucleic acid sequences.

Both cDNA and genomic sequences are suitable for eukaryotic expression, as the host cell will generally process the genomic transcripts to yield functional mRNA for translation into protein. Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude larger than the cDNA gene. However, the inventor does not exclude the possibility of employing a genomic version of a particular gene where desired.

As used herein, the terms "engineered" and "recombinant" cells are intended to refer to a cell into which an exogenous DNA segment or gene, such as a cDNA or gene has been introduced. Therefore, engineered cells are distinguishable from naturally occurring cells which do not contain a recombinantly introduced exogenous DNA segment or gene. Engineered cells are thus cells having a gene or genes introduced through the hand of man. Recombinant cells include those having an introduced cDNA or genomic DNA, and also include genes positioned adjacent to a promoter not naturally associated with the particular introduced gene.

To express a recombinant encoded protein or peptide, whether mutant or wild-type, in accordance with the present invention one would prepare an expression vector that comprises one of the claimed isolated nucleic acids under the control of one or more promoters. To bring a coding sequence "under the control of" a promoter, one positions the 5' end of the translational initiation site of the reading frame generally between about 1 and 50 nucleotides "downstream" of (i.e., 3' of) the chosen promoter. The "upstream" promoter stimulates transcription of the inserted DNA and promotes expression of the encoded recombinant protein. This is the meaning of "recombinant expression" in the context used here.

Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as *E. coli* and *B. subtilis* transformed with recombinant phage DNA, plasmid DNA or cosmid DNA expression vectors.

Certain examples of prokaryotic hosts are *E coli* strain RR1, *E. coli* LE392, *E. coli* B, *E. coli* X 1776 (ATCC No. 31537) as well as *E. coli* W3110 (F-, lambda-, prototrophic, ATCC No. 273325); bacilli such as *Bacillus subtilis;* and other enterobacteriaceae such as *Salmonella typhimurium, Serratia marcescens,* and various Pseudomonas species.

In general, plasmid vectors containing replicon and control sequences that are derived from species compatible with the host cell are used in connection with these hosts. The vector ordinarily carries a replication site, as well as marking sequences that are capable of providing phenotypic selection in transformed cells. For example, *E. coli* is often transformed using pBR322, a plasmid derived from an *E. coli* species. Plasmid pBR322 contains genes for ampicillin and tetracycline resistance and thus provides easy means for identifying transformed cells. The pBR plasmid, or other microbial plasmid or phage must also contain, or be modified to contain, promoters that can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector that can be used to transform host cells, such as *E. coli* LE392.

Further useful vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, or the like.

Promoters that are most commonly used in recombinant DNA construction include the b-lactamase (penicillinase), lactose and typtophan (trp) promoter systems. While these are the most commonly used, other microbial promoters have been discovered and utilized, and details concerning their nucleotide sequences have been published, enabling those of skill in the art to ligate them functionally with plasmid vectors.

For expression in Saccharomyces, the plasmid YRp7, for example, is commonly used (Stinchcomb et al., 1979; Kingsman et al., 1979; Tschemper et al., 1980). This plasmid contains the trpl gene, which provides a selection marker for a mutant strain of yeast lacking the ability to grow in tryptophan, for example ATCC No. 44076 or PEP4-1 (Jones, 1977). The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization.

In addition to micro-organisms, cultures of cells derived from multicellular organisms may also be used as hosts. In principle, any such cell culture is workable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing one or more coding sequences.

In a useful insect system, *Autograph californica* nuclear polyhidrosis virus (AcNPV) is used as a vector to express foreign genes. The virus grows in *Spodoptera frugiperda* cells. The isolated nucleic acid coding sequences are cloned into non-essential regions (for example the polyhedron gene) of the virus and placed under control of an AcNPV promoter (for example the polyhedron promoter). Successful insertion of the coding sequences results in the inactivation of the polyhedron gene and production of non-occluded recombinant virus (i.e., virus lacking the proteinaceous coat coded for by the polyhedron gene). These recombinant viruses are then used to infect *Spodoptera frugiperda* cells in which the inserted gene is expressed (e.g., U.S. Pat. No. 4,215,051).

Examples of useful mammalian host cell lines are VERO and HeLa cells, Chinese hamster ovary (CHO) cell lines, W138, BHK, COS-7,293, HepG2, 3T3, RIN and MDCK cell lines. In addition, a host cell may be chosen that modulates the expression of the inserted sequences, or modifies and processes the gene product in the specific fashion desired. Such modifications (e.g., glycosylation) and processing (e.g., cleavage) of protein products may be important for the function of the encoded protein.

Different host cells have characteristic and specific mechanisms for the post-translational processing and modification of proteins. Appropriate cell lines or host systems can be chosen to ensure the correct modification and processing of the foreign protein expressed. Expression vectors for use in mammalian cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter; the vaccinia virus 7.5K promoter). Further, it is also possible, and may be desirable, to utilize promoter or control sequences normally associated with the desired gene sequence, provided such control sequences are compatible with the host cell systems.

A number of viral based expression system may be utilized, for example, commonly used promoters are derived from polyoma, Adenovirus 2, cytomegalovirus and Simian Virus 40 (SV40). The early and late promoters of SV40 virus are useful because both are obtained easily from the virus as a fragment which also contains the SV40 viral origin of replication. Smaller or larger SV40 fragments may also be used, provided there is included the approximately 250 bp sequence extending from the HinDIII site toward the BglI site located in the viral origin of replication.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing proteins in infected hosts.

Specific initiation signals may also be required for efficient translation of the claimed isolated nucleic acid coding sequences. These signals include the ATG initiation codon and adjacent sequences. Exogenous translational control signals, including the ATG initiation codon, may additionally need to be provided. One of ordinary skill in the art would readily be capable of determining this need and providing the necessary signals. It is well known that the initiation codon must be in-frame (or in-phase) with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements or transcription terminators (Bittner et al., 1987).

In eukaryotic expression, one will also typically desire to incorporate into the transcriptional unit an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

For long-term, high-yield production of recombinant proteins, stable expression is preferred. For example, cell lines that stably express constructs encoding proteins may be engineered. Rather than using expression vectors that contain viral origins of replication, host cells can be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched medium, and then are switched to a selective medium. The selectable marker in the recombinant plasmid confers resistance to the selection and allows cells to stably integrate the plasmid into their chromosomes and grow to form foci, which in turn can be cloned and expanded into cell lines.

A number of selection systems may be used, including, but not limited, to the herpes simplex virus thymidine kinase (Wigler et al., 1977), hypoxanthine-guanine phosphoribosyltransferase (Szybalska et al., 1962) and adenine phosphoribosyltransferase genes (Lowy et al., 1980), in t$\bar{\text{k}}$, hgpr t or apr$\bar{\text{t}}$ cells, respectively. Also, antimetabolite resistance can be used as the basis of selection for dhfr, which confers resistance to methotrexate (Wigler et al., 1980; O'Hare et al., 1981); gpt, which confers resistance to mycophenolic acid (Mulligan et al., 1981); neo, which confers resistance to the aminoglycoside G-418 (Colberre-Garapin et al., 1981); and hygro, which confers resistance to hygromycin (Santerre et al., 1984).

It is contemplated that the isolated nucleic acids of the invention may be "overexpressed", i.e., expressed in increased levels relative to its natural expression in human prostate cells, or even relative to the expression of other proteins in the recombinant host cell. Such overexpression may be assessed by a variety of methods, including radiolabelling and/or protein purification. However, simple and direct methods are preferred, for example, those involving SDS/PAGE and protein staining or western blotting, followed by quantitative analyses, such as densitometric scanning of the resultant gel or blot. A specific increase in the level of the recombinant protein or peptide in comparison to the level in natural human prostate cells is indicative of overexpression, as is a relative abundance of the specific protein in relation to the other proteins produced by the host cell and, e.g., visible on a gel.

2. Purification of Expressed Proteins

Further aspects of the present invention concern the purification, and in particular embodiments, the substantial purification, of an encoded protein or peptide. The term "purified protein or peptide " as used herein, is intended to refer to a composition, isolatable from other components, wherein the protein or peptide is purified to any degree relative to its naturally-obtainable state, i.e., in this case, relative to its purity within a prostate cell extract. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50% or more of the proteins in the composition.

Various methods for quantifying the degree of purification of the protein or peptide will be known to those of skill in the art in light of the present disclosure. These include, for example, determining the specific activity of an active fraction, or assessing the number of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number". The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater -fold purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., Biochem. Biophys. Res. Comm., 76:425, 1977). It will therefore be appreciated that under differing electrophoresis conditions, the apparent molecular weights of purified or partially purified expression products may vary.

3. Antibody Generation

For some embodiments, it will be desired to produce antibodies that bind with high specificity to the protein product(s) of an isolated nucleic acid selected from the group comprising SEQ ID NO:1, SEQ ID NO:2, SEQ ID NO:3, SEQ ID NO:4, SEQ ID NO:5, SEQ ID NO:6, SEQ ID NO:7, Egr1 and DTDST. Means for preparing and characterizing antibodies are well known in the art (See, e.g., Antibodies: A Laboratory Manual, Cold Spring Harbor Laboratory, 1988; incorporated herein by reference).

Methods for generating polyclonal antibodies are well known in the art. Briefly, a polyclonal antibody is prepared by immunizing an animal with an antigenic composition and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobenzoyl-N-hydroxysuccinimide ester, carbodiimide and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, may also be given. The process of boosting and titering is repeated until a suitable titer is achieved. When a desired level of immunogenicity is obtained, the immunized animal can be bled and the serum isolated and stored, and/or in some cases the animal can be used to generate MAbs. For production of rabbit polyclonal antibodies, the animal can be bled through an ear vein or alternatively by cardiac puncture. The removed blood is allowed to coagulate and then centrifuged to separate serum components from whole cells and blood clots. The serum may be used as is for various applications or the desired antibody fraction may be purified by well-known methods, such as affinity chromatography using another antibody or a peptide bound to a solid matrix.

Monoclonal antibodies (MAbs) may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified expressed protein, polypeptide or peptide. The immunizing composition is administered in a manner that effectively stimulates antibody producing cells.

The methods for generating monoclonal antibodies (MAbs) generally begin along the same lines as those for preparing polyclonal antibodies. Rodents such as mice and rats are preferred animals, however, the use of rabbit, sheep or frog cells is also possible. The use of rats may provide certain advantages (Goding, 1986, pp. 60–61), but mice are preferred, with the BALB/c mouse being most preferred as this is most routinely used and generally gives a higher percentage of stable fusions.

The animals are injected with antigen as described above. The antigen may be coupled to carrier molecules such as keyhole limpet hemocyanin if necessary. The antigen would typically be mixed with adjuvant, such as Freund's complete or incomplete adjuvant. Booster injections with the same antigen would occur at approximately two-week intervals.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and have enzyme deficiencies that render them incapable of growing in certain selective media that support the growth of only the desired fused cells (hybridomas).

Any one of a number of myeloma cells may be used, as are known to those of skill in the art (Goding, pp. 65–66, 1986; Campbell, pp. 75–83, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods is also appropriate (Goding pp. 71–74, 1986).

Fusion procedures usually produce viable hybrids at low frequencies, about $1 \times 10^{-6}$ to $1 \times 10^{-8}$. However, this low frequency does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and thus they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which can then be propagated indefinitely to provide MAbs. The cell lines may be exploited for MAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. MAbs produced by either means may be further purified, if desired, using filtration, centrifugation and various chromatographic methods such as HPLC or affinity chromatography.

Large amounts of the monoclonal antibodies of the present invention may also be obtained by multiplying hybridoma cells in vivo. Cell clones are injected into mammals that are histocompatible with the parent cells, e.g., syngeneic mice, to cause growth of antibody-producing tumors. Optionally, the animals are primed with a hydrocarbon, especially oils such as pristane (tetramethylpentadecane) prior to injection.

In accordance with the present invention, fragments of the monoclonal antibody of the invention can be obtained from the monoclonal antibody produced as described above, by methods which include digestion with enzymes such as pepsin or papain and/or cleavage of disulfide bonds by chemical reduction. Alternatively, monoclonal antibody fragments encompassed by the present invention can be synthesized using an automated peptide synthesizer, or by expression of full-length gene or of gene fragments in *E. coli*.

The monoclonal conjugates of the present invention are prepared by methods known in the art, e.g., by reacting a monoclonal antibody prepared as described above with, for instance, an enzyme in the presence of a coupling agent such as glutaraldehyde or periodate. Conjugates with fluorescein markers are prepared in the presence of these coupling agents or by reaction with an isothiocyanate. Conjugates with metal chelates are similarly produced. Other moieties to which antibodies may be conjugated include radionuclides such as $^3$H, $^{125}$I, $^{131}$I $^{32}$P, $^{35}$S, $^{14}$C, $^{51}$Cr, $^{36}$Cl, $^{57}$Co, $^{58}$Co, $^{59}$Fe, $^{75}$Se, $^{152}$Eu, and $^{99m}$Tc, are other useful labels that can be conjugated to antibody. Radioactively labeled monoclonal antibodies of the present invention are produced according to well-known methods in the art. For instance, monoclonal antibodies can be iodinated by contact with sodium or potassium iodide and a chemical oxidizing agent such as sodium hypochlorite, or an enzymatic oxidizing agent, such as lactoperoxidase. Monoclonal antibodies according to the invention may be labeled with technetium-$^{99}$ by ligand exchange process, for example, by reducing pertechnate with stannous solution, chelating the reduced technetium onto a Sephadex column and applying the antibody to this column or by direct labelling techniques, e.g., by incubating pertechnate, a reducing agent such as $SNCl_2$, a buffer solution such as sodium-potassium phthalate solution, and the antibody.

It will be appreciated by those of skill in the art that monoclonal or polyclonal antibodies specific for proteins that are preferentially expressed in metastatic or nonmetastatic human prostate cancer will have utilities in several types of applications. These can include the production of diagnostic kits for use in detecting or diagnosing human prostate cancer. An alternative use would be to link such antibodies to therapeutic agents, such as chemotherapeutic agents, followed by administration to individuals with prostate cancer, thereby selectively targeting the prostate cancer cells for destruction. The skilled practitioner will realize that such uses are within the scope of the present invention.

E. Immunodetection Assays

1. Immunodetection Methods

In still further embodiments, the present invention concerns immunodetection methods for binding, purifying, removing, quantifying or otherwise generally detecting biological components. The encoded proteins or peptides of the present invention may be employed to detect antibodies having reactivity therewith, or, alternatively, antibodies prepared in accordance with the present invention, may be employed to detect the encoded proteins or peptides. The steps of various useful immunodetection methods have been described in the scientific literature, such as, e.g., Nakamura et al. (1987).

In general, the immunobinding methods include obtaining a sample suspected of containing a protein, peptide or antibody, and contacting the sample with an antibody or protein or peptide in accordance with the present invention, as the case may be, under conditions effective to allow the formation of immunocomplexes.

The immunobinding methods include methods for detecting or quantifying the amount of a reactive component in a sample, which methods require the detection or quantitation of any immune complexes formed during the binding process. Here, one would obtain of containing a prostate containing a prostate disease-marker encoded protein, peptide or a corresponding antibody, and contact the sample with an antibody or encoded protein or peptide, as the case may be, and then detect or quantify the amount of immune complexes formed under the specific conditions.

In terms of antigen detection, the biological sample analyzed may be any sample that is suspected of containing a prostate cancer-specific antigen, such as a prostate or lymph node tissue section or specimen, a homogenized tissue extract, an isolated cell, a cell membrane preparation, separated or purified forms of any of the above protein-containing compositions, or even any biological fluid that comes into contact with prostate tissues, including blood, lymphatic fluid, and even seminal fluid.

Contacting the chosen biological sample with the protein, peptide or antibody under conditions effective and for a period of time sufficient to allow the formation of immune complexes (primary immune complexes) is generally a matter of simply adding the composition to the sample and incubating the mixture for a period of time long enough for the antibodies to form immune complexes with, i.e., to bind to, any antigens present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any radioactive, fluorescent, biological or enzymatic tags or labels of standard use in the art. U.S. Patents concerning the use of such labels include, U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

The encoded protein, peptide or corresponding antibody employed in the detection may itself be linked to a detectable label, wherein one would then simply detect this label, thereby allowing the amount of the primary immune complexes in the composition to be determined.

Alternatively, the first added component that becomes bound within the primary immune complexes may be detected by means of a second binding ligand that has binding affinity for the encoded protein, peptide or corresponding antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labelled secondary antibodies or ligands, and the remaining label in the secondary immune complexes is then detected.

Further methods include the detection of primary immune complexes by a two step approach. A second binding ligand, such as an antibody, that has binding affinity for the encoded protein, peptide or corresponding antibody is used to form secondary immune complexes, as described above. After washing, the secondary immune complexes are contacted with a third binding ligand or antibody that has binding affinity for the second antibody, again under conditions effective and for a period of time sufficient to allow the formation of immune complexes (tertiary immune complexes). The third ligand or antibody is linked to a detectable label, allowing detection of the tertiary immune complexes thus formed. This system may provide for signal amplification if desired.

The immunodetection methods of the present invention have evident utility in the diagnosis of conditions such as prostate cancer and benign prostate hyperplasia. Here, a biological or clinical sample suspected of containing either the encoded protein or peptide or corresponding antibody is used. However, these embodiments also have applications to non-clinical samples, such as in the titering of antigen or antibody samples, in the selection of hybridomas, and the like.

In the clinical diagnosis or monitoring of patients with prostate cancer, the detection of an antigen encoded by a prostate cancer marker nucleic acid, or an increase in the levels of such an antigen, in comparison to the levels in a corresponding biological sample from a normal subject is indicative of a patient with prostate cancer. The basis for such diagnostic methods lies, in part, with the finding that the nucleic acid prostate cancer markers identified in the present invention are overexpressed in prostate cancer tissue samples (see Example 1 below). By extension, it can be inferred that at least some of these markers produce elevated levels of encoded proteins, that may also be used as prostate cancer markers.

Those of skill in the art are very familiar with differentiating between significant expression of a biomarker, which represents a positive identification, and low level or background expression of a biomarker. Indeed, background expression levels are often used to form a "cut-off" above which increased staining will be scored as significant or positive. Significant expression may be represented by high levels of antigens in tissues or within body fluids, or alternatively, by a high proportion of cells from within a tissue that each give a positive signal.

2. Immunohistochemistry

The antibodies of the present invention may also be used in conjunction with both fresh-frozen and formalin-fixed, paraffin-embedded tissue blocks prepared for study by immunohistochemistry (IHC). For example, each tissue block consists of 50 mg of residual "pulverized" prostate tumor. The method of preparing tissue blocks from these particulate specimens has been successfully used in previous IHC studies of various prognostic factors, e.g., in breast, and is well known to those of skill in the art (Brown et al., 1990; Abbondanzo et al., 1990; Allred et al., 1990).

Briefly, frozen-sections may be prepared by rehydrating 50 ng of frozen "pulverized" prostate tumor at room temperature in phosphate buffered saline (PBS) in small plastic capsules; pelleting the particles by centrifugation; resuspending them in a viscous embedding medium (OCT); inverting the capsule and pelleting again by centrifugation; snap-freezing in −70° C. isopentane; cutting the plastic capsule and removing the frozen cylinder of tissue; securing the tissue cylinder on a cryostat microtome chuck; and cutting 25–50 serial sections containing an average of about 500 remarkably intact prostate tumor cells.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and embedding the block in paraffin; and cutting up to 50 serial permanent sections.

3. ELISA

As noted, it is contemplated that the encoded proteins or peptides of the invention will find utility as immunogens, e.g., in connection with vaccine development, in immunohistochemistry and in ELISA assays. One evident utility of the encoded antigens and corresponding antibodies is in immunoassays for the detection of prostate disease marker proteins, as needed in diagnosis and prognostic monitoring.

Immunoassays, in their most simple and direct sense, are binding assays. Certain preferred immunoassays are the various types of enzyme linked immunosorbent assays (ELISA) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, antibodies binding to the encoded proteins of the invention are immobilized onto a selected surface exhibiting protein affinity, such as a well in a polystyrene microtiter plate. Then, a test composition suspected of containing the prostate disease marker antigen, such as a clinical sample, is added to the wells. After binding and washing to remove non-specifically bound immunocomplexes, the bound antibody may be detected. Detection is generally achieved by the addition of a second antibody specific for the target protein, that is linked to a detectable label. This type of ELISA is a simple "sandwich ELISA". Detection may also be achieved by the addition of a second antibody, followed by the addition of a third antibody that has binding affinity for the second antibody, with the third antibody being linked to a detectable label.

In another exemplary ELISA, the samples suspected of containing the prostate disease marker antigen are immobilized onto the well surface and then contacted with the antibodies of the invention. After binding and washing to remove non-specifically bound immunocomplexes, the bound antigen is detected. Where the initial antibodies are linked to a detectable label, the immunocomplexes may be detected directly. Again, the immunocomplexes may be detected using a second antibody that has binding affinity for the first antibody, with the second antibody being linked to a detectable label.

Another ELISA in which the proteins or peptides are immobilized, involves the use of antibody competition in the detection. In this ELISA, labelled antibodies are added to the wells, allowed to bind to the prostate disease marker protein, and detected by means of their label. The amount of marker antigen in an unknown sample is then determined by mixing the sample with the labelled antibodies before or during incubation with coated wells. The presence of marker antigen in the sample acts to reduce the amount of antibody available for binding to the well and thus reduces the ultimate signal. This is appropriate for detecting antibodies in an unknown sample, where the unlabeled antibodies bind to the antigen-coated wells and also reduces the amount of antigen available to bind the labeled antibodies.

Irrespective of the format employed, ELISAs have certain features in common, such as coating, incubating or binding, washing to remove non-specifically bound species, and detecting the bound immunecomplexes. These are described as follows:

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating of nonspecific adsorption sites on the immobilizing surface reduces the background caused by nonspecific binding of antisera to the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the control human prostate cancer and/or clinical or biological sample to be tested under conditions effective to allow immunecomplex (antigen/antibody) formation. Detection of the immunecomplex then requires a labeled secondary binding ligand or antibody, or a secondary binding ligand or antibody in conjunction with a labeled tertiary antibody or third binding ligand.

"Under conditions effective to allow immnunecomplex (antigen/antibody) formation" means that the conditions preferably include diluting the antigens and antibodies with solutions such as BSA, bovine gamma globulin (BGG) and phosphate buffered saline (PBS)/Tween. These added agents also tend to assist in the reduction of nonspecific background.

The "suitable" conditions also mean that the incubation is at a temperature and for a period of time sufficient to allow effective binding. Incubation steps are typically from about 1 to 2 to 4 hours, at temperatures preferably on the order of 25° to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immunecomplexes between the test sample and the originally bound material, and subsequent washing, the occurrence of even minute amounts of immunecomplexes may be determined.

To provide a detecting means, the second or third antibody will have an associated label to allow detection. Preferably, this label will be an enzyme that will generate color development upon incubating with an appropriate chromogenic substrate. Thus, for example, one will desire to contact and incubate the first or second immunecomplex with a urease, glucose oxidase, alkaline phosphatase or hydrogen peroxidase-conjugated antibody for a period of time and under conditions that favor the development of further immunecomplex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea and bromocresol purple or 2,2'-azido-di-(3-ethyl-benzthiazoline-6-sulfonic acid [ABTS] and $H_2O_2$, in the case of peroxidase as the enzyme label. Quantitation is then achieved by measuring the degree of color generation, e.g., using a visible spectra spectrophotometer.

4. Use of Antibodies for Radioimaging

The antibodies of this invention will be used to quantify and localize the expression of the encoded marker proteins. The antibody, for example, will be labeled by any one of a variety of methods and used to visualize the localized concentration of the cells producing the encoded protein. Such an assay also will reveal the subcellular localization of the protein, which can have diagnostic and therapeutic applications.

The invention also relates to an in vivo method of imaging a pathological prostate condition using the above described monoclonal antibodies. Specifically, this method involves administering to a subject an imaging-effective amount of a detectably-labeled prostate cancer-specific monoclonal antibody or fragment thereof and a pharmaceutically effective carrier and detecting the binding of the labeled monoclonal antibody to the diseased tissue. The term "in vivo imaging" refers to any method which permits the detection of a labeled monoclonal antibody of the present invention or fragment thereof that specifically binds to a diseased tissue located in the subject's body. A "subject" is a mammal, preferably a human. An "imaging effective amount" means that the amount of the detectably-labeled monoclonal antibody, or fragment thereof, administered is sufficient to enable detection of binding of the monoclonal antibody or fragment thereof to the diseased tissue.

A factor to consider in selecting a radionuclide for in vivo diagnosis is that the half-life of a nuclide must be long enough so that it is still detectable at the time of maximum uptake by the target, but short enough that deleterious radiation upon the host, as well as background, is minimized. Ideally, a radionuclide used for in vivo imaging will lack a particulate emission, but produce a large number of photons in a 140–2000 keV range, which may be readily detected by conventional gamma cameras.

A radionuclide may be bound to an antibody either directly or indirectly by using an intermediary functional group. Intermediary functional groups that are often used to bind radioisotopes that exist as metallic ions to antibody are diethylenetriaminepentaacetic acid (DTPA) and ethylene diaminetetraacetic acid (EDTA). Examples of metallic ions suitable for use in this invention are $^{99m}Tc$, $^{123}I$, $^{131}I$ $^{111}In$, $^{131}I$, $^{97}Ru$, $^{67}Cu$, $^{67}Ga$, $^{125}I$, $^{68}Ga$, $^{72}As$, $^{89}Zr$, and $^{201}Tl$.

In accordance with this invention, the monoclonal antibody or fragment thereof may be labeled by any of several techniques known to the art. The methods of the present invention may also use paramagnetic isotopes for purposes of in vivo detection. Elements particularly useful in Magnetic Resonance Imaging ("MRI") include $^{157}Gd$, $^{55}Mn$, $^{162}Dy$, $^{52}Cr$, and $^{56}Fe$.

Administration of the labeled antibody may be local or systemic and accomplished intravenously, intraarterially, via the spinal fluid or the like. Administration may also be intradermal or intracavitary, depending upon the body site under examination. After a sufficient time has lapsed for the monoclonal antibody or fragment thereof to bind with the diseased tissue, for example 30 minutes to 48 hours, the area of the subject under investigation is examined by routine imaging techniques such as MRI, SPECT, planar scintillation imaging or newly emerging imaging techniques. The exact protocol will necessarily vary depending upon factors specific to the patient, as noted above, and depending upon the body site under examination, method of administration and type of label used; the determination of specific procedures would be routine to the skilled artisan. The distribution of the bound radioactive isotope and its increase or decrease with time is then monitored and recorded. By comparing the results with data obtained from studies of clinically normal individuals, the presence and extent of the diseased tissue can be determined.

It will be apparent to those of skill in the art that a similar approach may be used to radio-image the production of the encoded prostate disease marker proteins in human patients. The present invention provides methods for the in vivo diagnosis of prostate cancer in a patient. Such methods generally comprise administering to a patient an effective amount of a prostate cancer specific antibody, to which antibody is conjugated a marker, such as a radioactive isotope or a spin-labeled molecule, that is detectable by non-invasive methods. The antibody-marker conjugate is allowed sufficient time to come into contact with reactive antigens that are present within the tissues of the patient, and the patient is then exposed to a detection device to identify the detectable marker.

5. Kits

In still further embodiments, the present invention concerns immunodetection kits for use with the immunodetection methods described above. As the encoded proteins or peptides may be employed to detect antibodies and the corresponding antibodies may be employed to detect encoded proteins or peptides, either or both of such components may be provided in the kit. The immunodetection kits will thus comprise, in suitable container means, an encoded protein or peptide, or a first antibody that binds to an encoded protein or peptide, and an immunodetection reagent.

In certain embodiments, the encoded protein or peptide, or the first antibody that binds to the encoded protein or peptide, may be bound to a solid support, such as a column matrix or well of a microtiter plate.

The immunodetection reagents of the kit may take any one of a variety of forms, including those detectable labels that are associated with or linked to the given antibody or antigen, and detectable labels that are associated with or attached to a secondary binding ligand. Exemplary secondary ligands are those secondary antibodies that have binding affinity for the first antibody or antigen, and secondary antibodies that have binding affinity for a human antibody.

Further suitable immunodetection reagents for use in the present kits include the two-component reagent that comprises a secondary antibody that has binding affinity for the first antibody or antigen, along with a third antibody that has binding affinity for the second antibody, the third antibody being linked to a detectable label.

The kits may further comprise a suitably aliquoted composition of the encoded protein or polypeptide antigen, whether labeled or unlabeled, as may be used to prepare a standard curve for a detection assay.

The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody or antigen may be placed, and preferably, suitably aliquoted. Where a second or third binding ligand or additional component is provided, the kit will also generally contain a second, third or other additional container into which this ligand or component may be placed. The kits of the present invention will also typically include a means for containing the antibody, antigen, and any other reagent containers in close confinement for commercial sale. Such containers may include injection or blow-molded plastic containers into which the desired vials are retained.

F. Detection and Quantitation of RNA Species

One embodiment of the instant invention comprises a method for identification of prostate cancer cells in a biological sample by amplifying and detecting nucleic acids corresponding to prostate cancer cell markers. The biological sample can be any tissue or fluid in which prostate cancer cells might be present. Various embodiments include bone marrow aspirate, bone marrow biopsy, lymph node aspirate, lymph node biopsy, spleen tissue, fine needle aspirate, skin biopsy or organ tissue biopsy. Other embodiments include samples where the body fluid is peripheral blood, lymph fluid, ascites, serous fluid, pleural effusion, sputum, cerebrospinal fluid, lacrimal fluid, stool or urine.

Nucleic acid used as a template for amplification is isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary DNA. In one embodiment, the RNA is whole cell RNA and is used directly as the template for amplification.

Pairs of primers that selectively hybridize to nucleic acids corresponding to prostate cancer-specific markers are contacted with the isolated nucleic acid under conditions that permit selective hybridization. Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced.

Next, the amplification product is detected. In certain applications, the detection may be performed by visual means. Alternatively, the detection may involve indirect identification of the product via chemiluminescence, radioactive scintigraphy of incorporated radiolabel or fluorescent label or even via a system using electrical or thermal impulse signals (Affymax technology; Bellus, 1994).

Following detection, one may compare the results seen in a given patient with a statistically significant reference group of normal patients and prostate cancer patients. In this way, it is possible to correlate the amount of marker detected with various clinical states.

1. Primers

The term primer, as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed. Primers may be provided in double-stranded or single-stranded form, although the single-stranded form is preferred.

2. Template Dependent Amplification Methods

A number of template dependent processes are available to amplify the marker sequences present in a given template sample. One of the best known amplification methods is the polymerase chain reaction (referred to as PCR) which is described in detail in U.S. Pat. Nos. 4,683,195, 4,683,202 and 4,800,159, and in Innis et al., 1990, each of which is incorporated herein by reference in its entirety.

Briefly, in PCR, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR amplification procedure may be performed in order to quantify the amount of mRNA amplified. Methods of reverse transcribing RNA into cDNA are well known and described in Sambrook et al., 1989. Alternative methods for reverse transcription utilize thermostable, RNA-dependent DNA polymerases. These methods are described in WO 90/07641 filed Dec. 21, 1990. Polymerase chain reaction methodologies are well known in the art.

Another method for amplification is the ligase chain reaction ("LCR"), disclosed in EPA No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention, Walker et al., Proc. Nat'l Acad. Sci. USA 89:392–396 (1992), incorporated herein by reference in its entirety.

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in GB Application No. 2 202 328, and in PCT Application No. PCT/US89/01025, each of which is incorporated herein by reference in its entirety, may be used in accordance with the present invention. In the former application, "modified" primers are used in a PCR-like, template- and enzyme-dependent synthesis. The primers may be modified by labelling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labelled probe signals the presence of the target sequence.

Other nucleic acid amplification procedures include transcription-based amplification systems (TAS), including nucleic acid sequence based amplification (NASBA) and 3SR (Kwoh et al., Proc. Nat'l Acad. Sci USA 86:1173 (1989); Gingeras et al., PCT Application WO 88/10315, incorporated herein by reference in their entirety). In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by an RNA polymerase such as T7 or SP6. In an isothermal cyclic reaction, the RNA's are reverse transcribed into single stranded DNA, which is then converted to double stranded DNA, and then transcribed once again with an RNA polymerase such as T7 or SP6. The resulting products, whether truncated or complete, indicate target specific sequences.

Davey et al., EPA No. 329 822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of E. coli DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, M. A., In: PCR PROTOCOLS: A GUIDE TO METHODS AND APPLICATIONS, Academic Press, N.Y., 1990; Ohara et al., *Proc. Nat'l Acad. Sci. USA,* 86:5673–5677, 1989; each herein incorporated by reference in their entirety).

Methods based on ligation of two (or more) oligonucleotides in the presence of nucleic acid having the sequence of the resulting "di-oligonucleotide", thereby amplifying the dioligonucleotide, may also be used in the amplification step of the present invention. Wu et al., *Genomics* 4:560 (1989), incorporated herein by reference in its entirety.

3. Separation Methods

Following amplification, it may be desirable to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook et al., 1989.

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982).

4. Identification Methods

Amplification products must be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled, nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by Southern blotting and hybridization with a labeled probe. The techniques involved in Southern blotting are well known to those of skill in the art and can be found in many standard books on molecular protocols. See Sambrook et al., 1989. Briefly, amplification products are separated by gel electrophoresis. The gel is then contacted with a membrane, such as nitrocellulose, permitting transfer of the nucleic acid and non-covalent binding. Subsequently, the membrane is incubated with a chromophore-conjugated probe that is capable of hybridizing with a target amplification product. Detection is by exposure of the membrane to x-ray film or ion-emitting detection devices.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

6 Kit Components

All the essential materials and reagents required for detecting prostate cancer cells in a biological sample may be assembled together in a kit. This generally will comprise preselected primers for specific markers. Also included may be enzymes suitable for amplifying nucleic acids including various polymerases (RT, Taq, etc.), deoxynucleotides and buffers to provide the necessary reaction mixture for amplification.

Such kits generally will comprise, in suitable means, distinct containers for each individual reagent and enzyme as well as for each marker primer pair. Preferred pairs of primers for amplifying nucleic acids are selected to amplify the sequences specified in SEQ ID NO:1, SEQ ID NO:2, SEQ ID NO:3, SEQ ID NO:4, SEQ ID NO:5, SEQ ID NO:6, or SEQ ID NO:7, along with the cDNAs for Egr1 or DTDST.

In another embodiment, such kits will comprise hybridization probes specific for cancer markers, chosen from a group including nucleic acids corresponding to the sequences specified in SEQ ID NO:1, SEQ ID NO:2, SEQ ID NO:3, SEQ ID NO:4, SEQ ID NO:5, SEQ ID NO:6 and SEQ ID NO:7, along with the cDNAs for Egr1 and DTDST Such kits generally will comprise, in suitable means, distinct containers for each individual reagent and enzyme as well as for each marker hybridization probe.

G. Use of RNA Fingerprinting to Identify Markers of Prostate Disease

RNA fingerprinting is a means by which RNAs isolated from many different tissues, cell types or treatment groups can be sampled simultaneously to identify RNAs whose relative abundances vary. Two forms of this technology were developed simultaneously and reported in 1992 as RNA fingerprinting by differential display (Liang and Pardee, 1992; Welsh et al., 1992). (See also Liang and Pardee, U.S. Pat. No. 5,262,311, incorporated herein by reference in its entirety.) Some of the experiments described herein were performed similarly to Donahue et al., *J Biol. Chem.* 269: 8604–8609, 1994.

All forms of RNA fingerprinting by PCR are theoretically similar but differ in their primer design and application. The most striking difference between differential display and other methods of RNA fingerprinting is that differential display utilizes anchoring primers that hybridize to the poly A tails of mRNAs. As a consequence, the PCR products amplified in differential display are biased towards the 3' untranslated regions of mRNAs.

The basic technique of differential display has been described in detail (Liang and Pardee, 1992). Total cell RNA is primed for first strand reverse transcription with an anchoring primer composed of oligo dT and any two of the four deoxynucleosides. The oligo dT primer is extended using a reverse transcriptase, for example, Moloney Murine Leukemia Virus (MMLV) reverse transcriptase. The synthesis of the second strand is primed with an arbitrarily chosen oligonucleotide, using reduced stringency conditions. Once the double-stranded cDNA has been synthesized, amplification proceeds by standard PCR techniques, utilizing the same primers. The resulting DNA fingerprint is analyzed by gel electrophoresis and ethidium bromide staining or autoradiography. A side by side comparison of fingerprints obtained from tumor versus normal tissue samples using the same oligonucleotide primers identifies mRNAs that are differentially expressed.

RNA fingerprinting technology has been demonstrated as being effective in identifying genes that are differentially expressed in cancer (Liang et al., 1992; Wong et al., 1993; Sager et al., 1993; Mok et al., 1994; Watson et al., 1994; Chen et al., 1995; An et al., 1995). The present invention utilizes the RNA fingerprinting technique to identify genes that are differentially expressed in human prostate cancer.

H. Design and Theoretical Considerations for Relative Quantitative RT-PCR

Reverse transcription (RT) of RNA to cDNA followed by relative quantitative PCR (RT-PCR) can be used to determine the relative concentrations of specific MRNA species isolated from normal, benign and cancerous prostate tissues. By determining that the concentration of a specific mRNA species varies, it is shown that the gene encoding the specific mRNA species is differentially expressed. This technique can be used to confirm that MRNA transcripts shown to be differentially regulated by RNA fingerprinting are differentially expressed in prostate cancer progression.

In PCR, the number of molecules of the amplified target DNA increase by a factor approaching two with every cycle of the reaction until some reagent becomes limiting. Thereafter, the rate of amplification becomes increasingly diminished until there is no increase in the amplified target between cycles. If a graph is plotted in which the cycle number is on the X axis and the log of the concentration of the amplified target DNA is on the Y axis, a curved line of characteristic shape is formed by connecting the plotted points. Beginning with the first cycle, the slope of the line is positive and constant. This is said to be the linear portion of the curve. After a reagent becomes limiting, the slope of the line begins to decrease and eventually becomes zero. At this point the concentration of the amplified target DNA becomes asymptotic to some fixed value. This is said to be the plateau portion of the curve.

The concentration of the target DNA in the linear portion of the PCR amplification is directly proportional to the starting concentration of the target before the reaction began. By determining the concentration of the amplified products of the target DNA in PCR reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived can be determined for the respective tissues or cells. This direct proportionality between the concentration of the PCR products and the relative mRNA abundances is only true in the linear range of the PCR reaction.

The final concentration of the target DNA in the plateau portion of the curve is determined by the availability of reagents in the reaction mix and is independent of the original concentration of target DNA. Therefore, the first condition that must be met before the relative abundances of a MRNA species can be determined by RT-PCR for a collection of RNA populations is that the concentrations of the amplified PCR products must be sampled when the PCR reactions are in the linear portion of their curves.

The second condition that must be met for an RT-PCR experiment to successfully determine the relative abundances of a particular MRNA species is that relative concentrations of the amplifiable cDNAs must be normalized to some independent standard. The goal of an RT-PCR experiment is to determine the abundance of a particular MRNA species relative to the average the relative abundance of other mRNAs are compared.

Most protocols for competitive PCR utilize internal PCR standards that are approximately as abundant as the target. These strategies are effective if the products of the PCR amplifications are sampled during their linear phases. If the products are sampled when the reactions are approaching the plateau phase, then the less abundant product becomes relatively over represented. Comparisons of relative abundances made for many different RNA samples, such as is the case when examining RNA samples for differential expression, become distorted in such a way as to make differences in relative abundances of RNAs appear less than they actually are. This is not a significant problem if the internal standard is much more abundant than the target. If the internal standard is more abundant than the target, then direct linear comparisons can be made between RNA samples.

The above discussion describes theoretical considerations for an RT-PCR assay for clinically derived materials. The problems inherent in clinical samples are that they are of variable quantity (making normalization problematic), and that they are of variable quality (necessitating the co-amplification of a reliable internal control, preferably of larger size than the target). Both of these problems are overcome if the RT-PCR is performed as a relative quantitative RT-PCR with an internal standard in which the internal standard is an amplifiable cDNA fragment that is larger than the target cDNA fragment and in which the abundance of the mRNA encoding the internal standard is roughly 5–100 fold higher than the mRNA encoding the target. This assay measures relative abundance, not absolute abundance of the respective mRNA species.

Other experiments described below were performed using a more conventional relative quantitative RT-PCR assay with an external standard protocol. These assays sample the PCR products in the linear portion of their amplification curves. The number of PCR cycles that are optimal for sampling must be empirically determined for each target cDNA fragment. In addition, the reverse transcriptase products of each RNA population isolated from the various tissue samples must be carefully normalized for equal concentrations of amplifiable cDNAs. This consideration is very important since the assay measures absolute mRNA abundance. Absolute mRNA abundance can be used as a measure of differential gene expression only in normalized samples. While empirical determination of the linear range of the amplification curve and normalization of cDNA preparations are tedious and time consuming processes, the resulting RT-PCR assays can be superior to those derived from the relative quantitative RT-PCR assay with an internal standard.

One reason for this advantage is that without the internal standard/competitor, all of the reagents can be converted into a single PCR product in the linear range of the amplification curve, thus increasing the sensitivity of the assay. Another reason is that with only one PCR product, display of the product on an electrophoretic gel or another display method becomes less complex, has less background and is easier to interpret.

I. Diagnosis and Prognosis of Human Cancer

In certain embodiments, the present invention allows the diagnosis and prognosis of human prostate cancer by screening for marker nucleic acids. The field of cancer diagnosis and prognosis is still uncertain. Various markers have been proposed to be correlated with metastasis and malignancy. They can be classified generally as cytologic, protein or nucleic acid markers.

Cytologic markers include "nuclear roundedness" (Diamond et al., 1982) and cell ploidy. Protein markers include prostate specific antigen (PSA) and CA125. Nucleic acid markers include amplification of Her2/neu, point mutations in the p53 or ras genes, and changes in the sizes of triplet repeat segments of particular chromosomes.

All of these markers exhibit certain drawbacks associated with false positives and false negatives. A false positive result occurs when an individual without malignant cancer exhibits the presence of a "cancer marker". For example, elevated serum PSA has been associated with prostate carcinoma. However, it also occurs in some individuals with non-malignant, benign hyperplasia of the prostate. A false negative result occurs when an individual actually has cancer, but the test fails to show the presence of a specific marker. The incidence of false negatives varies for each marker, and frequently also by tissue type.

Additional problems arise when a marker is present only within the transformed cell itself. Ras point mutations can only be detected within the mutant cell, and are apparently not present in, for example, the blood serum or urine of individuals with ras-activated carcinomas. This means that, in order to detect a malignant tumor, one must take a sample of the tumor itself, or of its metastatic cells. Since the object of cancer detection is to identify and treat tumors before they metastasize, it becomes necessary to first identify and sample a tumor before the presence of the cancer marker can be detected.

Finally, specific problems occur with markers that are present in normal cells but absent in 5 cancer cells. Most tumor samples will contain mixed populations of both normal and transformed cells. If one is searching for a marker that is present in normal cells, but occurs at reduced levels in transformed cells, the "background" signal from the normal cells in the sample may mask the presence of transformed cells.

The ideal cancer marker would be one that is present in malignant cancers, and either missing or else expressed at significantly lower levels in benign tumors and normal cells. Further, since any single marker would typically be present only in some proportion of malignant cancers, it is better to have a number of such markers for each cancer type. The present invention addresses this need for prostate cancer by identifying several new nucleic acid markers that are expressed at higher levels in malignant prostate carcinoma than in benign or normal prostate. In particular, the results for markers E22B39 and DTDST, discussed in Example 1 below, are quite promising in that these markers are apparently only overexpressed in malignant tumors and are present at lower levels in benign or normal prostate. Further, these markers are elevated in a high percentage of human prostate cancers examined to date.

It is anticipated that in clinical applications, human tissue samples will be screened for the presence of the markers of prostate disease identified herein. Such samples could consist of needle biopsy cores, surgical resection samples, lymph node tissue, or serum. In certain embodiments, nucleic acids would be extracted from these samples and amplified as described above. Some embodiments would utilize kits containing pre-selected primer pairs or hybridization probes. The amplified nucleic acids would be tested for the markers by, for example, gel electrophoresis and ethidium bromide staining, or Southern blotting, or a solid-phase detection means as described above. These methods are well known within the art. The levels of selected markers detected would be compared with statistically valid groups of metastatic, non-metastatic malignant, benign or normal prostate samples. The diagnosis and prognosis of the individual patient would be determined by comparison with such groups.

Another embodiment of the present invention involves application of RT-PCR techniques to detect circulating prostate cancer cells (i.e., those that have already metastasized), using probes and primers selected from a group consisting of SEQ ID NO:1, SEQ ID NO:2, SEQ ID NO:3, SEQ ID NO:4, SEQ ID NO:5, SEQ ID NO:6, SEQ ID NO:7, Egr1 and DTDST. Similar techniques have been described in PCT Patent Application No. WO 94/10343, incorporated herein by reference.

In this embodiment, metastatic prostate cancer cells are detected in hematopoietic samples by amplification of prostate cancer-specific nucleic acid sequences. Samples taken from blood or lymph nodes are treated as described below to purify total cell RNA. The isolated RNA is reverse transcribed using a reverse transcriptase and primers selected to bind under high stringency conditions to a nucleic acid sequence from a group consisting of SEQ ID NO:1, SEQ ID NO:2, SEQ ID NO:3, SEQ ID NO:4, SEQ ID NO:5, SEQ ID NO:6, SEQ ID NO:7, Egr1 and DTDST. Following reverse transcription, the resulting cDNAs are amplified using standard PCR techniques (described below) and a thermostable DNA polymerase.

The presence of amplification products corresponding to prostate cancer-marker nucleic acids can be detected by several alternative means. In one embodiment, the amplification product can be detected by gel electrophoresis and ethidium bromide staining. Alternatively, following the gel electrophoresis step the amplification product can be detected by standard Southern blotting techniques, using a hybridization probe selected to bind specifically to a prostate cancer-marker nucleic acid sequence. Probe hybridization may in turn be detected by a standard labeling means, for example, by incorporation of [$^{32}$P]-nucleotides followed by autoradiography. The amplification products may alternatively be detected using a solid phase detection system as described above, utilizing a prostate cancer-marker specific hybridization probe and an appropriate labelling means. The presence of prostate cancer-marker nucleic acids in blood or lymph node samples can be taken as indicative of a patient with metastatic prostate cancer.

J. Targeted Inhibition of Prostate Cancer Markers

In principle, the prostate cancer markers identified in the present invention can serve as targets for therapeutic intervention in prostate cancer. For example, E22B135 has been reported to encode a putative sulfate transporter (See Hastbacka et al, 1994; Wallis, 1995). Individuals who are homozygous for mutations in this gene fail to sulfate their proteoglycans to the same extent as heterozygous or normal individuals. This metabolic deficiency results in affected individuals suffering a form of dwarfism which is accompanied by bone pattern defects. Other organ systems are not affected, and if the skeletal development is sufficient to permit ventilation of the lungs and closure of the spine, affected individuals live normal life spans. While a large number of tissues produce this putative sulfate transporter, only bone is pathologically affected by its defect or absence.

Prostate tumor cells appear to over produce this sulfate transporter. This over expression would be predicted to result in an increased production of sulfated proteoglycans by tumorigenic cells. Prostate cancer cells have an unusual tendency to metastasize to bone. These two observations, bone abnormalities in diastrophic dysplasia and prostate cancer bone tropism, may result from opposite extremes of a single metabolic mechanism, the level of expression of the E22B135 encoding sulfate transporter. If so, blocking or disrupting the diastrophic dysplasia sulfate transporter and/ or proteoglycan sulfating metabolism in general would prevent or reduce metastasis of prostate cancer to bone.

It may also be true that blocking or disrupting the diastrophic dysplasia sulfate transporter and/or proteoglycan sulfating metabolism in general would prevent or reduce the ability of prostate cancer tumors to grow or propagate in bone. If this hypothesis is true, then an entirely novel pathway for the treatment of prostate cancer becomes evident; blocking or disrupting the diastrophic dysplasia sulfate transporter and/or proteoglycan sulfating metabolism in general to prevent or reduce metastasis and/or tumor growth of prostate cancer. Since no other organ system is pathologically affected by the disruption of the diastrophic dysplasia sulfate transporter there would be little toxicity to other organs in the body except bones. Bones would be expected to be affected but, since victims of diastrophic dysplasia live normal life spans and maintain at least a minimally functional skeleton all of their lives, the expected toxicity to bones of this proposed treatment may be acceptable to patients with metastatic prostate cancer. Furthermore, dependence on an active sulfate transporter may be reduced in adult men since bone metabolism slows substantially with age.

Potential inhibitors of sulfate transporters include DIDS (4,4'-diisothiocyano-2,2' disulfonic acid stilbene) (Silberg et al., 1995), phenylglyoxal, niflumic acid, dinitrofluorobenzene or 1,2-cyclohexanedione (Koetters et al., 1995), salicylic acid (Darling et al., 1994), and tetrachlorosalicylanilide (Kreke et al., 1995). Such inhibitors can have utility as therapeutic agents for the treatment of prostate cancer. The skilled practitioner will realize that prostate cancer treatment targeted towards inhibition of the E22B135-encoded protein, along with other proteins encoded by the claimed prostate disease markers, are included within the scope of the present invention.

Inhibitors could also potentially be designed for the previously unreported prostate cancer markers identified in the present invention. This approach is complicated by the fact that no specific function has been identified for most of these gene products, and no data is available on their three-dimensional structures.

Identification of protein function can be extrapolated, in some cases, from the primary sequence data, provided that sequence homology exists between the unknown protein and a protein of similar sequence and known function. Proteins tend to occur in large families of relatively similar sequence and function. For example, a number of the serine proteases, like trypsin and chymotrypsin, have extensive sequence homologies and relatively similar three-dimensional structures. Other general categories of homologous proteins include different classes of transcription factors, membrane receptor proteins, tyrosine kinases, GTP-binding proteins, etc. The putative amino acid sequences encoded by the prostate cancer marker nucleic acids of the present invention can be cross-checked for sequence homologies versus the protein sequence database of the National Biomedical Research Fund. Homology searches are a standard technique for the skilled practitioner.

Even three-dimensional structure can be inferred from the primary sequence data of the encoded proteins. Again, if homologies exist between the encoded amino acid sequences and other proteins of known structure, then a model for the structure of the encoded protein can be designed, based upon the structure of the known protein. An example of this type of approach was reported by Ribas de Pouplana and Fothergill-Gilmore (Biochemistry 33: 7047–7055, 1994). These authors developed a detailed three-dimensional model for the structure of Drosophila alcohol dehydrogenase, based in part upon sequence homology with the known structure of 3-a, 20-β-hydroxysteroid dehydrogenase. The predicted three-dimensional structure can be further refined by well known computerized analyses, such as provided by energy minimization programs. Once a three-dimensional model is available, inhibitors can be designed by standard computer modeling techniques. This area has been recently reviewed by Sun and Cohen (Gene 137:127–132, 1993), herein incorporated by reference.

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the particular embodiments that are disclosed and still obtain a like or similar result without departing from the spirit and scope of the invention.

K. Experimental Materials and Methods

1. Application of RNA fingerprinting to discover biomarkers for prostate cancers RNA fingerprinting (Liang and Pardee, 1992; Liang and Pardee, 1993) was applied to nucleic acids isolated from two normal prostate glands and four Stage B prostate tumors with Gleason grade at or near five. After the tissue samples were frozen and ground to a powder in liquid nitrogen, total cell RNA was isolated by the guanidinium thiocyanate method (Chomczynski and Sacchi, 1987).

After RNA isolation, the nucleic acids were precipitated with ethanol. The precipitates were pelleted by centrifugation and redissolved in water. The redissolved nucleic acids were then digested with RNase-free DNase I (Boehringer Mannheim, Inc.) after the manufacturer's instructions, followed by organic extraction with phenol:chloroform:isoamyl alcohol (25:24:1) and reprecipitation with ethanol. Polyadenylated RNA was purified from this total RNA fraction by column chromatography on oligo-dT cellulose, according to standard protocols (Sambrook et al., 1989).

Polyadenylated RNA was pelleted by centrifugation and redissolved in water. The purity and concentration of the RNA in solution was estimated by determining optical density at wave lengths of 260 nm and 280 nm (Sambrook et al., 1989). A small aliquot of the RNA was also separated by gel electrophoresis in a 3% formaldehyde gel with MOPS buffer (Sambrook et al., 1989) to confirm the estimation of concentration.

The differential display experiments followed the protocol of Liang and Pardee (1992) except that it was modified by using 5' biotinylated primers for non-isotopic PCR product detection. In these experiments, 0.2 mg of polyadenylated RNA was primed for reverse transcription with an anchoring primer composed of oligo dT. Twelve anchoring primer oligonucleotides of the general structure $T_{11}XY$ were synthesized (where X=C, G or A, and Y=C, G, A, or T). These anchoring primers were used to prime first strand cDNA synthesis during the reverse transcription step of a differential display protocol. Sixteen additional arbitrarily chosen 10-mer oligonucleotides of defined sequence were also synthesized to prime second strand synthesis of the cDNA. There are 192 combinations of anchoring and arbitrary primers. All combinations were utilized on all prostate specimens in these experiments.

Reverse transcription was performed with 200 units of MMLV (Moloney Murine Leukemia Virus) reverse transcriptase (GIBCO/BRL) in the presence of 50 mM Tris-HCl (pH 8.3), 75 mM KCl, 3 mM $MgCl_2$, 10 mM DTT, 500 mM dNTP, 200 nM arbitrary decamer, 1 mM anchored primer and 1 U/ml RNase inhibitor. The reaction mixture was incubated at room temperature for 10 minutes, then at 37° C. for 50 minutes. After reverse transcription the enzyme was denatured by heating to 65° C. for 10 minutes.

One tenth of the resulting reverse transcription reaction products was then amplified by PCR using the same anchoring primer and arbitrarily chosen oligonucleotide as used in the reverse transcription step. The PCR reaction contained 10 mM Tris-HCl (pH 8.3), 50 mM KCl, 20 mM dNTP, 1.5 mM $MgCl_2$, 200 nM arbitrary decamer, 1 mM biotinylated anchored primer, [$^{35}$S]dATP and 1 unit of Taq DNA polymerase (Boehringer Mannheim) in a 40 ml volume. The amplification was performed in a thermal cycler (MJ Research) for 30 cycles with denaturing at 94° C. for 30 sec, annealing at 40° C. for 2 min, and extending at 72° C. for 30 sec.

The PCR products were then separated on a 6% TBE-urea sequencing gel (Sambrook et al., 1989) and detected by autoradiograph. Differentially appearing PCR products were excised from the gels, reamplified using the same primers used in the original amplification, and cloned using the TA cloning strategy (Invitrogen, Inc. and Promega, Inc.).

2. Confirmation of Differential Expression by Relative Quantitative RT-PCR: Protocols for RT-PCR a Reverse transcription Five mg of polyadenylated RNA from each tissue sample was reverse transcribed into cDNA. Reverse transcription was performed with 400 units of MMLV reverse transcriptase (GIBCO/BRL) in the presence of 50 mM Tris-HCl (pH8.3), 75 mM KCl, 3 mM $MgCl_2$, 10 mM DTT, 500 mM dNTP, 50 ng random hexamers per microgram of RNA, and 1 U/ml RNase inhibitor. The reaction volume was 60 ml. The reaction mixture was incubated at room temperature for 10 minutes, then at 37° C. for 50 minutes. After reverse transcription the enzyme was denatured by heating to 65° C. for 10 minutes. After heat denaturation the samples were diluted with water to a final volume of 300 ml.

Experimental designs were performed utilizing RT-PCR to examine mRNAs for differential expression. The sequences of oligonucleotides used as primers to direct the amplification of the various cDNA fragments are presented in Table 2.

b. Relative Quantitative RT-PCR With an Internal Standard

The concentrations of the original total cell RNAs were determined by measurement of $OD_{260/280}$ (Sambrook et al., 1989) and confirmed by examination of ribosomal RNAs on ethidium bromide stained agarose gels. It is required that all quantitative PCR reactions be normalized for equal amounts of amplifiable cDNA after the reverse transcription is completed. One solution to this problem is to terminate the reactions before driving the PCR reactions into the plateau phase. This approach was utilized in some studies because it is quick and efficient. Lipocortin II was used as the internal standard or competitor. These PCRs were set up as follows: Reagents: 200 mM each dNTP, 200 nM each oligonucleotide primer, 1×PCR buffer (Boehringer Mannheim including 1.5 mM $MgCl_2$), 3 ml diluted cDNA, and 2.5 units of Taq DNA polymerase/ 100 ml of reaction volume.

Cycling parameters: 30 cycles of 94° C. for 1 min; 55° C. for 1 min; and 72° C. for two min. Thermocyclers were either the MJ research thermocycler or the Stratagene Robocycler.

C. Relative Quantitative RT-PCR with an External Standard

There are three problems with the relative quantitative RT-PCR strategy described above. First, the internal standard must be roughly 4–10 times more abundant that the target for this strategy to normalize the samples. Second, because most of the PCR products are templated from the more abundant internal standard, the assay is less than optimally sensitive. Third, the internal standard must be truly unvarying. The result is that while the strategy described above is fast, convenient and applicable to samples of varying quality, it lacks sensitivity to modest changes in abundances.

To address these issues, a normalization was performed using both the β-actin and asparagine synthetase mRNAs as external standards. These PCR reactions were performed with sufficient cycles to observe the products in the linear range of their amplification curves. Photographic negatives of gels of ethidium bromide stained PCR products were produced for each experiment. These negatives were scanned and quantified using a BioRad densitometer. The quantified data was then normalized for variations in the starting concentrations of amplifiable cDNA by comparing the quantified data from each experiment with that derived from a similar experiment that amplified a cDNA fragment copied from the β-actin MRNA. Quantified data that had been normalized to β-actin were converted into bar graph representations.

L. EXAMPLES

Example 1

Identification of Markers of Prostate Disease by Use of RNA Fingerprinting

The differential display protocol, as described above, was performed on polyadenylated RNAs isolated from two normal prostate glands and four Stage B prostate tumors. All 192 combinations of anchoring and arbitrarily selected primers were utilized for each sample. Each reaction generated 50 to 100 discreet bands of PCR product. Therefore, approximately 10,000 to 20,000 PCR products were generated for each RNA sample.

Only those bands that appeared differentially in both normal prostate samples and all four tumors were selected for further analysis. There were 250 such differentially appearing PCR products. Northern blot analysis indicated that only 12.5% of these clones were differentially expressed (data not shown). A review of the original DNA fingerprints permitted the reduction of likely candidates to 44 PCR products. These were cloned and sequenced. The nucleotide sequences of cloned PCR products were determined by dideoxy termination sequencing using the TaqTrack sequencing system (Promega Corporation) and the SeqLight nonisotopic detection kit (Tropix, Inc).

These 44 clones were further selected based on two criteria: 1) DNA sequence determination demonstrating a known gene with a likely function related to cancer, or 2) dramatic differences in steady state abundances as revealed by northern blots. Nine gene products were chosen for further analysis. The sequences of these gene products are identified in the Sequence Listing below, incorporated herein by reference. The mRNAs for E18B3 (SEQ ID NO:1), E22B120 (SEQ ID NO:2) and E22B134 (SEQ ID NO:3) were more abundant in normal prostate glands than in prostate tumors. The mRNAs for E22B39 (SEQ ID NO:4), E22B49 (SEQ ID NO:5), E18B43 (SEQ ID NO:6) and E22B135 (SEQ ID NO: 7) were more abundant in tumors than in normal prostate glands.

The differential expression of several of the cloned PCR products was further examined by relative quantitative RT-PCR. Total cell RNA was isolated from two grossly normal prostate glands (N), four prostate glands with BPH (benign prostate hyperplasia) (B), five prostate glands with tumors (T), a lymph node metastasis (LM) of a prostate tissue, and a needle core biopsy of a prostate gland known to contain a tumor (NB). A no-template control was also performed (NC). All cDNAs were normalized for similar amounts of β-actin cDNA by RT-PCR. RT-PCR products were electrophoresed through agarose.

For relative quantitative RT-PCR with an external standard, quantitation was performed by examining a photographic negative of the ethidium bromide stained gels using a densitometer. A normalizing statistic was generated for each cDNA sample, as the average of all β-actin signals divided by the β-actin signal for each cDNA sample respectively. Data for each experimental sample was then normalized by multiplying the observed densitometry observation by the individual normalizing statistics. Normalized values predict differences in the steady state abundances of the respective mRNAs in the original total cell RNA samples.

The results of relative quantitative RT-PCR with an external standard confirm that E22B135 (FIG. 1) and E22B39 (FIG. 2) are up regulated in prostate cancer. Other experiments (not shown) demonstrated that β-actin and asparagine synthetase are not differentially regulated in prostate tumors.

At the time of this application, comparison of the sequence data with Genbank showed that E22B3, 39, 49, 99, 104, 120, and 134 are previously unreported genes. Additional studies showed that the gene encoding E22B49 is adjacent to the Bat II gene. It appears that this gene is expressed in cells of the immune system that are frequently present in the prostate.

Figure 3:
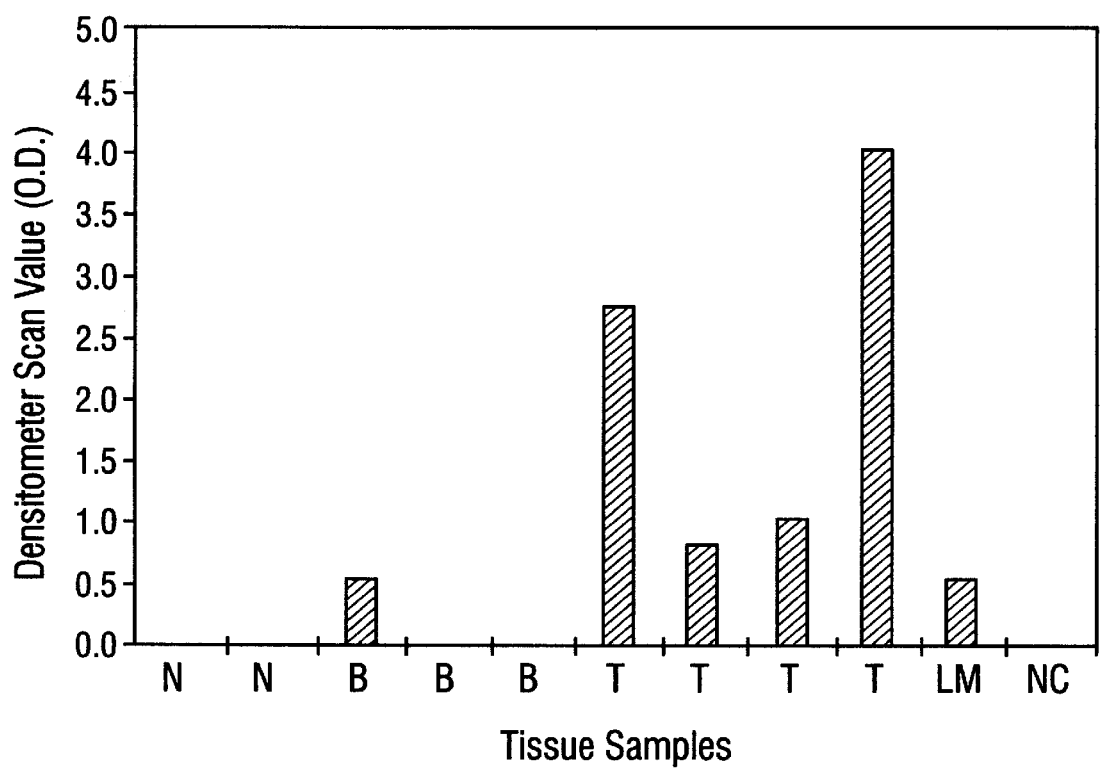
FIG. 3. Normalized quantitative RT-PCR of hEGR1, encoding the protein corresponding to GenBank accession number P18146 shows overexpression in prostate cancers compared to normal prostate and benign prostatic hyperplasia. Abbreviations are as described in the legend to FIG. 1.

The sequence of E22B43 was found to be identical with Egr1 (Early Growth Response Gene 1). Relative quantitative RT-PCR confirmed that the steady state abundance of the mRNA encoding Egr1 is significantly increased in prostate tumors as compared to normal and benign glands (FIG. 3).

E22B135 is encoded by a gene that is mutated in diastrophic dysplasia (Hastbacka et al., 1994). It is widely expressed in many tissues including the prostate. A relative quantitative RT-PCR experiment conclusively demonstrated that E22B135 is up regulated in prostate tissues (FIG. 1). This gene encodes a putative sulfate transporter (Hastbacka et al., 1994; Wallis, 1995).

E22B3, E22B120 and E22B134 are previously undescribed gene products that appear to be derived from mRNAs with greater steady state abundances in normal prostate glands than in tumors. These three are candidates for suppressors of transformation. RT-PCR analysis was not performed on these gene products because tumors, being a mixture of normal and transformed cell types, may partially mask a reduced expression level of a particular MRNA species within a subpopulation of cells.

Figure 2:
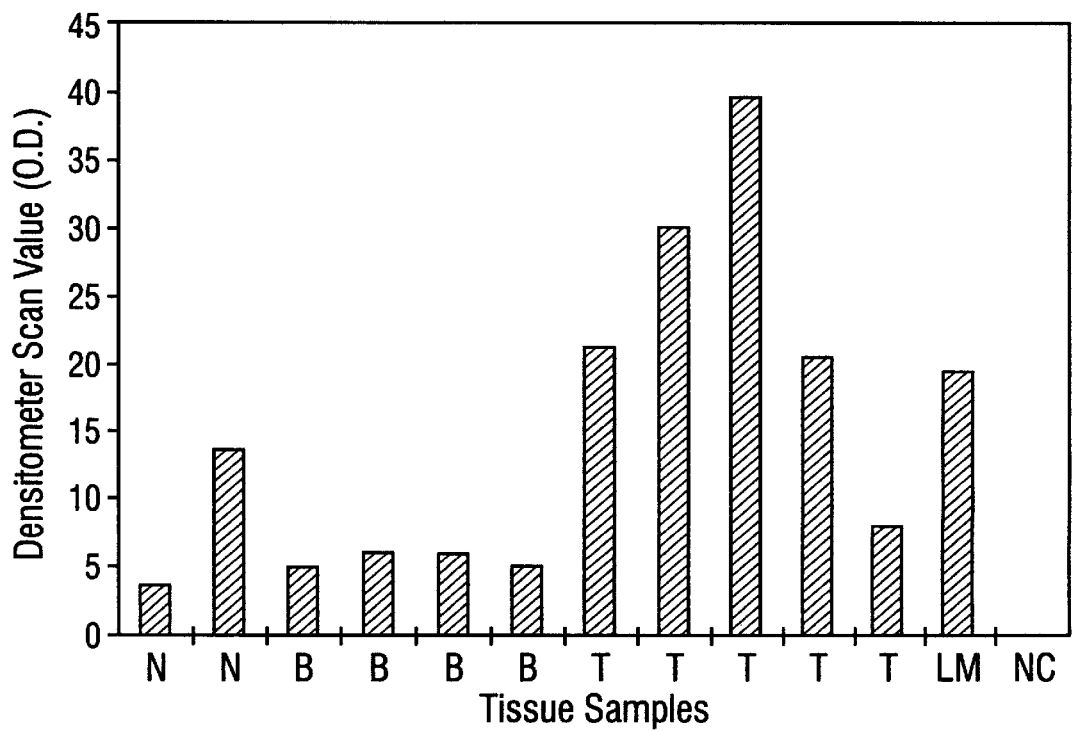
FIG. 2. Normalized quantitative RT-PCR of E22B39 shows overexpression in prostate cancers compared to normal prostate and benign prostatic hyperplasia. Abbreviations are as described in the legend to FIG. 1.

E22B39 appears to be a novel gene product whose MRNA abundance is greater in tumors than in normal and benign tissues (FIG. 2). Northern blots, RT-PCR experiments and examination of various cDNA clones reveal that there are multiple forms of the MRNA from which Band 39 was derived. There is clearly more than one polyadenylation site and possible alternatively spliced products. This gene is over expressed in prostate tumors (FIG. 2). This characteristic makes the Band 39 gene a likely candidate as a diagnostic biomarker for prostate cancer as well as a possible target of therapeutic intervention.

Those skilled in the art will realize that all processed forms of the E22B39 mRNA and its translation product(s) and antibodies that recognize the translation product(s) are included within the scope of the present invention. The genes and gene products (RNAs and proteins) for all of the above described markers of prostate disease or normal prostate are included within the scope of the invention herein described. Those experienced in the art will also recognize that the diagnosis and prognosis of prostatic cancer by detection of the nucleic acid and/or protein products of these genes are included within the scope of the present invention.

TABLE 1

Genes Whose mRNAs have Abundances that Vary in Prostate Cancer Relative to Normal and Benign Glands

| Name of cDNA Fragment | Sequence Determined | Confirmed by RT-PCR | Previously Known |
|---|---|---|---|
| Band 3 | YES | NO | NO |
| Band 39 | YES | YES | NO |
| Band 43 | YES | YES | Egr1 |
| Band 49 | YES | NO | NO |
| Band 99 | YES | NO | NO |
| Band 104 | YES | NO | NO |
| Band 120 | YES | NO | NO |
| Band 134 | YES | NO | NO |
| Band 135 | YES | YES | DTDST |

TABLE 2

Oligonucleotides used in the relative quantitative RT-PCR portion of these studies.
Oligonucleotides used to examine the expression of genes:

Band 39 (unknown gene)(two primer sets were designed)
   5' CCAGGATCCA GCATTTTGCT GCTTTATCAA AATGG 3', SEQ ID NO: 8
   5' ACCGGTACCT CACAAGGAGC TGTGAATGAG G 3', SEQ ID NO: 9
   and
   5' CCGCCGTCCT TCAATTTTCT TCACACTATC AACA 3', SEQ ID NO: 10
   5' GTCGGTGGTA TCTCCTAGTA ACCAAACCTA CA 3', SEQ ID NO: 11
Band 43 (Egr1)
   5' ATGGCCGCGGCCAAGGCCGAGATGC 3', SEQ ID NO: 12
   5' AGGGTAGGCAGGAGGCGGGTACTGGAG 3', SEQ ID NO: 13
Band 135 (Diastrophic dysplasia)
   5' CATCCTGAGA GCCAGCCTGA CATTAGA 3', SEQ ID NO: 14
   5' CCTCCTGCAT AATAGCTTTA GGTGACTTGA AGA 3', SEQ ID NO: 15

TABLE 2-continued

Oligonucleotides used in the relative quantitative RT-PCR portion of these studies.
Oligonucleotides used to examine the expression of genes:

Controls used to normalize relative quantitative RT-PCR
β-actin
   5' CGAGCTGCCTGACGGCCAGGTCATC 3', SEQ ID NO: 16
   5' GAAGCATTTGCGGTGGACGATGGAG 3', SEQ ID NO: 17
Asparagine Synthetase (AS)
   5' ACATTGAAGCACTCCGCGAC 3', SEQ ID NO: 18
   5' AGAGTGGCAGCAACCAAGCT 3', SEQ ID NO: 19

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention.

More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

M. REFERENCES

The following literature citations as well as those cited above are incorporated in pertinent part by reference herein for the reasons cited in the above text.

Antibodies: A Laboratory Manual, Cold Spring Harbor Laboratory, Cold Spring Harbor Press, Cold Spring Harbor, N.Y., 1988.
Abbondanzo et al., Breast Cancer Res. Treat., 16:182(#151), 1990.
Alcaraz et al., Cancer Res., 55:3998–4002, 1994.
Allred et al., Breast Cancer Res. Treat., 16:182(#149), 1990.
An et al., Proc. Amer. Assn. Canc. Res., 36:82, 1995.
Bellus, J Macromol. Sci. Pure Appl. Chem, A31(1):1355–1376, 1994.
Bittner et al., Methods in Enzymol, 153:516–544, 1987.
Bookstein et al., Science, 247:712–715, 1990a.
Bookstein et al., Proc. Nat'l Acad. Sci. USA 87:7762–7767, 1990b.
Boring et al., CA-Cancer J Pract., 43:7–26, 1993.
Bova et al., Cancer Res., 53:3869–3873, 1993.
Brown et al., Breast Cancer Res. Treat., 16:192(#191), 1990.
Campbell, In: Monoclonal Antibody Technology, Laboratory Techniques in Biochemistry and Molecular Biology, Burden and Von Knippenberg, Eds., Vol. 13:75–83, Elsevier, Amsterdam, 1984.
Capaldi et al., Biochem. Biophys. Res. Comm., 76:425, 1977
Carter et al., Proc. Nat'l Acad. Sci. USA, 87:8751–8755, 1990.
Carter and Coffey, In: J. P. Karr and H. Yamanak (eds.), Prostate Cancer: The Second Tokyo Symposium, pp. 19–27, New York: Elsevier, 1989.
Carter and Coffey, Prostate, 16:39–48, 1990
Chen et al., Proc. Am. Urol. Assn., 153:267A, 1995.
Chinault and Carbon, Gene, 5:111–126, 1979.
Chomczynski and Sacchi, Anal. Biochem., 162:156–159, 1987.
Colberre-Garapin et al., J Mol. Biol., 150:1, 1981.
Darling et al., Drug Metab. Dispos., 22: 318–323, 1994.
Davey et al., EPO No. 329 822.
Dbom, J. Cancer Res. Clin. Oncol., 106: 210–218, 1983.
Diamond et al., J. Urol., 128: 729–734, 1982.
Donahue et al., J. Biol. Chem., 269: 8604–8609, 1994.
Freifelder, Physical Biochemistry Applications to Biochemistry and Molecular Biology, 2nd ed. Wm. Freeman and Co., New York, N.Y., 1982.
Frohlich et al., Molec. Cell. Biol., 10: 3216–3223, 1990
Frohman, PCR PROTOCOLS: A GUIDE TO METHODS AND APPLICATIONS, Academic Press, N.Y., 1990.
Gefter et al., Somatic Cell Genet., 3: 231–236, 1977.
Gingeras et al., PCT Application WO 88/10315.
Goding, In: Monoclonal Antibodies: Principles and Practice, 2d ed., Orlando, Fla., Academic Press, pp. 60–61, 65–66, 71–74, 1986.
Hastbacka et al., Cell, 78:1073–1087, 1994.
Hess et al., J. Adv. Enzyme Reg., 7:149, 1968.
Hitzeman et al., J. Biol. Chem., 255:2073, 1980.
Holland et al., Biochemistry, 17:4900, 1978.
Innis et al., PCR Protocols, Academic Press, Inc., San Diego Calif., 1990.
Inouye et al., Nucleic Acids Res., 13:3101–3109, 1985.
Isaacs et al., Seminars in Oncology, 21:1–18, 1994.
Isaacs et al., Cancer Res., 51:4716–4720, 1991.
Johnson et al., In: BIOTECHNOLOGY AND PHARMACY, Pezzuto et al., Eds., Chapman and Hall, New York, 1993.
Jones, Genetics, 85:12, 1977.
Kingsman et al., Gene, 7:141, 1979.
Koetters et al., Biochim. Biophys. A., 1235:79–84, 1995.
Kohler and Milstein, Nature, 256:495–497, 1975.
Kohler and Milstein, Eur. J. Immunol, 6:511–519, 1976.
Kreke et al., Arch. Microbiol., 163:307–309, 1995.
Kwoh et al., Proc. Nat. Acad. Sci. USA, 86:1173, 1989.
Liang and Pardee, Science, 257:967–971, 1992.
Liang and Pardee, U.S. Pat. No. 5,262,311, 1993.
Liang et al., Cancer Res., 52: 6966–6968, 1992.
Lowy et al., Cell, 22: 817, 1980.
Macoska et al., Cancer Res., 54: 3824–3830, 1994.
Miller et al., PCT Application WO 89/06700.
Mok et al., Gynecol. Oncol., 52:247–252, 1994.
Morton et al., Cancer, 71:3737–3743, 1993.
Morton et al., Cancer Res., 53:3585–3590, 1993.
Morton et al., In: CANCER MEDICINE (3rd Ed.), Holland, J. F., Frei III, E., Bast Jr., C. C. (eds). Lea and Febiger, Philadelphia, Pa., pp. 1793–1824, 1993.
Mulligan et al., Proc. Nat'l Acad. Sci. USA, 78:2072, 1981.
Nakamura et al., In: Handbook of Experimental Immunology (4th Ed.), Weir, E., Herzenberg, L. A., Blackwell, C., Herzenberg, L. (eds). Vol. 1, Chapter 27, Blackwell Scientific Publ., Oxford, 1987.
O'Hare et al., Proc. Nat'l Acad. Sci. USA, 78:1527, 1981.
Ohara et al., Proc. Nat'l Acad. Sci. USA, 86:5673–5677, 1989.

Partin et al., *Cancer Res.,* 53:744–746, 1993.
Pearsons et al., *J. Urol.,* 150:120–125, 1993.
Ribas de Pouplana and Fothergill-Gilmore *Biochemistry,* 33:7047–7055, 1994.
Sager et al., *FASEB J.,* 7:964–970, 1993.
Sambrook et al., (ed.). *MOLECULAR CLONING.* Cold Spring Harbor Laboratory Press, Cold Spring Harbor, N.Y., 1989.
Scott et al., *Molec. Cell. Biol.,* 13:2247–2257, 1993
Slamon et al., *Science,* 224:256–262, 1984.
Smith, U.S. Pat. No. 4,215,051
Stinchcomb et al., *Nature,* 282:39, 1979.
Sun and Cohen, *Gene,* 137:127–132, 1993
Szybalska et al., *Proc. Nat'l Acad. Sci. USA,* 48:2026, 1962.
Takahashi et al., *Cancer Res.,* 54:3574–3579, 1994.
Tschemper et al., *Gene,* 10:157, 1980.
Umbas et al., *Cancer Res.,* 52:5104–5109, 1992.
Visakorpi et al., *Am. J. Pathol.,* 145:1–7, 1994.
Walker et al., *Proc. Nat'l Acad. Sci. USA,* 89:392–396, 1992.
Wallis, *Curr. Biol.,* 5:225–227, 1995.
Watson et al., *Cancer Res.,* 54:4598–4602, 1994.
Webb and Lin, *Invest. Urol.,* 17:401–404, 1980.
Welsh et al., *Nucleic Acids Res.,* 20:4965–4970, 1992.
Welsh and McClelland, *Nucl. Acids. Res.,* 18:7213–7218, 1990.
Wigler et al., *Cell,* 11:223, 1977.
Wigler et al., *Proc. Nat'l Acad. Sci. USA,* 77:3567, 1980.
Wong et al., *Int. J. Oncol.,* 3: 13–17, 1993.
Wu et al., *Genomics,* 4:560, 1989.

What is claimed is:

1. An isolated nucleic acid segment comprising the contiguous, full-length sequence of or a sequence fully complementary to SEQ ID NO:1, SEQ ID NO:3, SEQ ID NO:4 or SEQ ID NO:7.

2. The isolated nucleic acid segment of claim 1, further defined as comprising the contiguous, full-length sequence of or a sequence fully complementary to SEQ ID NO:1.

3. The isolated nucleic acid segment of claim 1, further defined as comprising the contiguous, full-length sequence of or a sequence fully complementary to SEQ ID NO:3.

4. The isolated nucleic acid segment of claim 1, further defined as comprising the contiguous, full-length sequence of or a sequence fully complementary to SEQ ID NO:4.

5. The isolated nucleic acid segment of claim 1, further defined as comprising the contiguous, full-length sequence of or a sequence fully complementary to SEQ ID NO:7.

6. An isolated nucleic acid segment comprising between 20 and about 100 contiguous bases from SEQ ID NO:1, SEQ ID NO:3, SEQ ID NO:4 or SEQ ID NO:7 or a fully complementary sequence of the same length.

7. A formulation comprising:
(a) an oligonucleotide pair, wherein said pair is effective to prime the polymerase chain reaction amplification of a nucleic acid segment comprising a sequence of SEQ ID NO:1, SEQ ID NO:3, SEQ ID NO:4, SEQ ID NO:6 or SEQ ID NO:7, wherein said formulation is used to detect prostate cancer cells in a biological sample; and
(b) a container for each oligonucleotide in said pair.

8. A formulation comprising:
(a) an oligonucleotide probe which hybridizes under high stringency conditions to a nucleic acid segment of SEQ ID NO:1, SEQ ID NO:3, SEQ ID NO:4, SEQ ID NO:6 or SEQ ID NO:7, wherein said formulation is used to detect prostate cancer cells in a biological sample; and
(b) a container for storage of said probe.

9. A formulation comprising:
(a) the oligonucleotide of SEQ ID NO:12 or SEQ ID NO:13 wherein said formulation is used to detect prostate cancer cells in a biological sample, and
(b) a container for storage of said oligonucleotide.

10. The formulation of claim 9, wherein said oligonucleotide is the oligonucleotide of SEQ ID NO:12.

11. The formulation of claim 9, wherein said oligonucleotide is the oligonucleotide of SEQ ID NO:13.

12. A formulation comprising the oligonucleotide pair of SEQ ID NO:12 and SEQ ID NO:13 wherein said formulation is used in the detection of prostate cancer cells in a biological sample.

13. The formulation of claim 12, wherein said detection is by polymerase chain reaction amplification.

14. A formulation for use in detecting prostate cancer cells in a biological sample, comprising:
(a) an oligonucleotide pair, wherein each oligonucleotide of said pair is at least thirty bases long, wherein said pair is effective to prime the polymerase chain reaction amplification of a nucleic acid segment comprising a sequence of SEQ ID NO:5; and
(b) a container for each oligonucleotide in said pair.

15. A formulation comprising:
(a) an oligonucleotide probe of at least 30 bases in length which hybridizes under high stringency conditions to a nucleic acid segment of SEQ ID NO:5, wherein said formulation is used to detect prostate cancer cells in a biological sample; and
(b) a container for storage of said probe.

* * * * *

UNITED STATES PATENT AND TRADEMARK OFFICE
CERTIFICATE OF CORRECTION

PATENT NO.    :   5,861,248

DATED         :   January 19, 1999

INVENTOR(S)   :   David W. Russell and Anice E. Thigpen

It is certified that error appears in the above-identified patent and that said Letters Patent is hereby corrected as shown below:

Title page, item [73], delete "Urocor, Inc., Oklahoma City, Okla." and insert --Board of Regents, The University of Texas System, Austin, Tex.-- therefor.

Signed and Sealed this

Twenty-ninth Day of June, 1999

*Attest:*

Q. TODD DICKINSON

*Attesting Officer*　　　*Acting Commissioner of Patents and Trademarks*